(12) United States Patent
Balbierz

(10) Patent No.: US 6,770,070 B1
(45) Date of Patent: Aug. 3, 2004

(54) LUNG TREATMENT APPARATUS AND METHOD

(75) Inventor: Daniel J. Balbierz, Redwood City, CA (US)

(73) Assignee: R. ITA Medical Systems, Inc., Mountain View, CA (US)

( * ) Notice: Subject to any disclaimer, the term of this patent is extended or adjusted under 35 U.S.C. 154(b) by 0 days.

(21) Appl. No.: 09/527,906

(22) Filed: Mar. 17, 2000

(51) Int. Cl.[7] .............................................. A61B 18/18
(52) U.S. Cl. ........................... 606/41; 600/566; 606/28
(58) Field of Search ........................... 606/27, 28, 213, 606/214, 41, 45, 48–50; 600/566, 567

(56) References Cited

U.S. PATENT DOCUMENTS

| | | | |
|---|---|---|---|
| 4,565,200 A | 1/1986 | Cosman | |
| 4,799,494 A | 1/1989 | Wang | |
| 4,893,635 A | 1/1990 | Degroot et al. | |
| 5,056,529 A | 10/1991 | Degroot | |
| 5,156,151 A | * 10/1992 | Imran et al. ................. | 600/374 |
| 5,314,466 A | 5/1994 | Stern et al. | |
| 5,322,503 A | 6/1994 | Desai | |
| 5,328,467 A | 7/1994 | Edwards et al. | |
| 5,334,193 A | * 8/1994 | Nardella ....................... | 606/41 |
| 5,334,206 A | 8/1994 | Daikuzono | |
| 5,336,222 A | 8/1994 | Durgin, Jr. et al. | |
| 5,342,357 A | 8/1994 | Nardella | |
| 5,370,675 A | * 12/1994 | Edwards et al. ............. | 607/101 |
| 5,403,311 A | 4/1995 | Abele et al. | |
| 5,470,308 A | 11/1995 | Edwards et al. | |
| 5,536,267 A | 7/1996 | Edwards et al. | |
| 5,551,426 A | 9/1996 | Hummel et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,560,358 A | 10/1996 | Arnold et al. | |
| 5,562,703 A | 10/1996 | Desai | |
| 5,599,345 A | 2/1997 | Edwards et al. | |
| 5,599,346 A | 2/1997 | Edwards et al. | |
| 5,607,389 A | 3/1997 | Edwards et al. | |
| 5,620,481 A | 4/1997 | Desai et al. | |
| 5,685,839 A | 11/1997 | Edwards et al. ............... | 604/22 |
| 5,701,895 A | * 12/1997 | Prutchi et al. ............... | 128/630 |
| 5,718,237 A | 2/1998 | Haaga | |
| 5,749,895 A | 5/1998 | Sawyer et al. | |
| 5,810,804 A | 9/1998 | Gough et al. | |
| 5,827,276 A | 10/1998 | LeVeen et al. | |
| 5,855,576 A | 1/1999 | LeVeen et al. | |
| 5,868,740 A | 2/1999 | LeVeen et al. | |
| 5,879,349 A | 3/1999 | Edwards | |
| 5,957,919 A | 9/1999 | Laufer | |
| 6,003,517 A | * 12/1999 | Sheffield et al. ............ | 128/898 |
| 6,016,809 A | 1/2000 | Mulier et al. | |
| 6,022,362 A | 2/2000 | Lee et al. | |
| 6,033,401 A | * 3/2000 | Edwards et al. ............. | 606/41 |
| 6,106,524 A | * 8/2000 | Eggers et al. ................. | 606/50 |
| 6,200,333 B1 | 3/2001 | Laufer | |
| 6,261,241 B1 | * 7/2001 | Burbank et al. ............. | 600/564 |
| 6,287,304 B1 | * 9/2001 | Eggers et al. ................. | 606/37 |
| 6,440,130 B1 | 8/2002 | Mulier et al. | |
| 6,613,048 B2 | 9/2003 | Mulier et al. | |

FOREIGN PATENT DOCUMENTS

| | | | |
|---|---|---|---|
| DE | 21 24 684 A2 | 11/1972 | |
| WO | WO94/10925 | 5/1994 | |
| WO | WO95/19142 | 7/1995 | |
| WO | WO 96/29946 | 10/1996 | ........... A61B/17/39 |
| WO | WO 97/06855 | 2/1997 | ........... A61N/1/40 |

* cited by examiner

*Primary Examiner*—Michael Peffley
(74) *Attorney, Agent, or Firm*—Jacqueline F. Mahoney; Peter J. Dehlinger; Perkins Coie LLP

(57) ABSTRACT

A method and apparatus for obtaining a lung biopsy with an apparatus capable of sealing tears within the lung and pleural space to reduce the risk of pneumothorax or pulmonary hemorrhage. The apparatus includes an RF ablation apparatus having a lung biopsy device an energy delivery device including at least one electrode designed to be deployed into target lung tissue, and a sensor. A closure device is operatively coupled to the elongated member to produce an immediate tight seal and promote healing at the tissue interface. A feedback control device is operatively coupled to the sensor and a RF source for controlling energy delivered to the electrodes.

72 Claims, 31 Drawing Sheets

Long Bevel Point

Short Bevel Point

V-Point

J-Point

Conical Point

Angled Conical Point

45° Needle Point

Trocar Point

Ring Electrodes

Ball Electrode

Hemispherical Electrode

Cylindrical Electrode

Conical Electrode

Needle Electrode

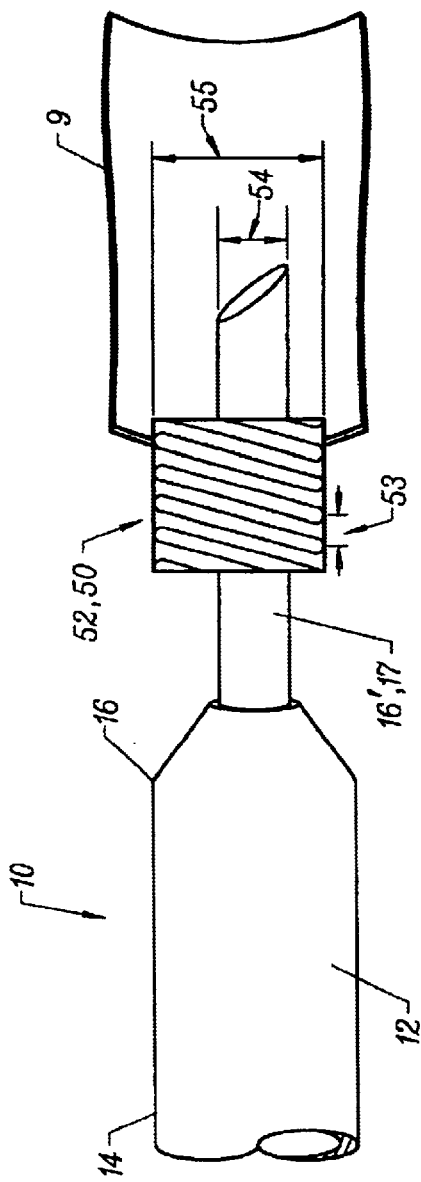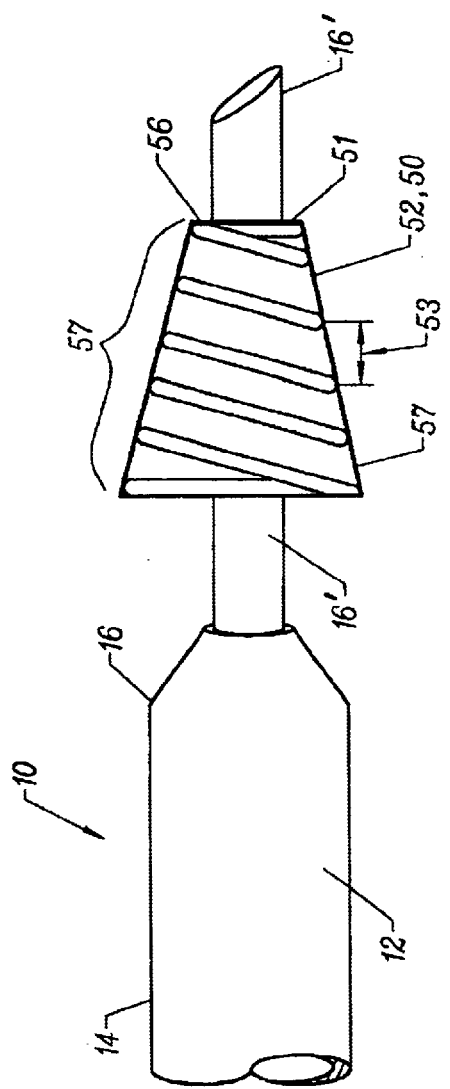
FIG. 22A
FIG. 22B

LUNG TREATMENT APPARATUS AND METHOD

CROSS-REFERENCE TO RELATED APPLICATIONS

BACKGROUND OF THE INVENTION

1. Field of the Invention

This invention relates generally to a method of obtaining a lung biopsy sample using minimally invasive methods. More particularly, the invention relates to a method of obtaining a lung biopsy sample percutaneously with a reduced risk of pneumothorax. Still more particularly, the invention relates to an apparatus and method for obtaining a lung biopsy sample and reliably sealing the entry path into the lung to reduce the risk of pneumothorax. Still more particularly the invention relates to an apparatus and method for obtaining a lung biopsy sample and sealing the entry path into the lung via the delivery of thermal energy to a target tissue site or use of a polymer sealant or mechanical closure device.

2. Description of the Related Art

The lungs are the organs for respiration in mammals. They have a set of unique material properties adapted to this function including elasticity, porosity and a large amount of surface area for gaseous exchange to efficiently oxygenate and remove waste gases from the blood. In the adult human, each lung is 25 to 30 cm (10 to 12 in) long and roughly conical. The left lung is divided into two sections or lobes: the superior and the inferior. The right lung is somewhat larger than the left lung and is divided into three lobes: the superior, middle, and inferior. These lobes are divided by the oblique and horizontal fissures. The left lung only has two lobes, an upper and lower. These lobes are divided by the oblique fissure. Both lungs are further divided by bronchopulmonary segments.

The two lungs are separated by a structure called the mediastinum, which contains the heart, trachea, esophagus, and blood vessels. Both right and left lungs are covered by an external membrane called the pleura. The outer layer of the pleura forms the lining of the chest cavity. The inner pleura covers each lung. A vacuum is maintained between these membranes that causes the lungs to expand during inhalation as the diaphragm muscle is pulled down causing the chest cavity to expand.

While the structure of the lung is extremely well suited as a respiratory organ at the same time it makes them susceptible to damage and disease from environmental factors by trapping disease causing pollutants within the structure of the lung. Due to the spread of western industrialized society, factors such as increasing concentrations of air pollution and incidents of smoking are resulting in a worldwide increase in the incidence of lung disease. Smokers and people who live in cities are exposed to substantial levels of carcinogenic air pollutants such as benzene and polycyclic aromatic hydrocarbons (PAHs). Two of the more prevalent disease resulting from these and other risk factors include emphysema and lung cancer. Lung cancer is a particularly insidious and deadly lung disease and each year it kills more Americans than any other type of cancer.

A key factor in the prevention and successful treatment of lung disease is early detection. One of the best tools available to the physician in this regard is the taking of a lung tissue sample or lung biopsy. In fact, biopsy is often necessary or otherwise highly advantageous as an adjunct to other diagnostic methods to improve diagnostic accuracy. Efforts to biopsy the lung have focused on three key requirements: 1) The need to harvest adequate tissue from an organ that is mostly air; 2) the need to obtain a biopsy specimen from within the lung tissue without permitting air to leak either from the outside or from the lung into the pleural space; and 3) the need to have access to the entire volume of the lung. The two currently practiced methods for lung biopsy: transbronchial biopsy and percutaneous biopsy have not been able to adequately address all three needs. In fact, both methods have significant clinical issues and technical drawbacks.

In particular, both methods present the risk of a potentially lifethreatening complication known as pneumothorax due to puncture of the lung by the biopsy needle. A pneumothorax is a collapse of the lung that occurs when the airtight integrity of the lining of the chest cavity (the pleural membrane) is broken due to a penetrating injury or a complication of a lung disease. This causes air to enter and collect in the pleural cavity (which is normally in a partial state of vacuum), collapsing the lung and severely, if not totally, impairing its function. The risk of this complication is considerable, potentially life-threatening and requires immediate medical intervention including surgery to vent air from the chest cavity. A recent ten year study has shown that the risk of pneumothorax for both fine needle biopsy and percutaneous biopsy is 11.7% (Greif J, et al. Percutaneous core needle biopsy vs. fine needle aspiration in diagnosing benign lung lesions Acta Cytol 1999 September–October; 43(5):756–60).

During the procedure of transbronchial biopsy a flexible fiberoptic bronchoscope is employed as a conduit through which a biopsy instrument is passed from the outside of the patient through the airways of the lung into the lung tissue. The use of fiberoptic devices for collecting tissue samples is done as part of a procedure known as fiberscopic-bronchoscopy which is a visual examination of the bronchial tubes. The bronchoscope, which is inserted down the trachea and into the bronchial tubes, has lighting and magnifying devices that enable the physician to see the bronchial surface. During this procedure the physician can obtain samples of cells for later microscopic examination. However, accessing the lung tissue biopsy site via the throat has the drawbacks of requiring that the patient be intubated (a sometimes difficult and time-consuming process) and put under general anesthesia (which increases mortality and morbidity). These and other factors result in the procedure taking considerable time, one to two hours, and burdening the patient with considerable expense due to required personal, equipment and facilities. Also due to size limitations, the distal end of many bronchoscopes, particularly rigid bronchoscopes, cannot be passed any further than the beginning of the segmental bronchi of the lower lobes of the lung. Thus, inaccessibility of significant portions of the lung is another key limitation of transbronchial procedures. Further, the procedure can result in air entering into the pleural space causing partial or complete pneumothorax.

Percutaneous needle biopsy involves introducing a biopsy needle (known as a transthoracic needle) through the chest wall usually after making a small skin incision. This procedure is often necessary, as many areas of the lung are too inaccessible to bronchoscopy, particularly areas abutting the chest wall. However, while the procedure provides increased accessibility and shorter procedure times versus transbronchial procedures, it has significant clinical risks and limited diagnostic accuracy. These risks include pneumothorax, and vessel perforation causing embolism and/or uncontrollable hemorrhage. Pneumothorax in percutaneous biopsy can result from either lung perforation or accidental suction of air into the chest during stylet changes. Pneumothorax is a likely event in percutaneous biopsy due to the sizable injury of the pleural membrane frequently resulting from this procedure.

Depending upon the patient, these risks may be so great that invasive surgical procedures such as open lung biopsy are preferred and/or are the only option. This is the case for patients who are receiving anticoagulants such as coumadin, making them particularly susceptible to uncontrollable pulmonary hemorrhage from inadvertent vessel perforation or other trauma by the biopsy needle. Further, percutaneous biopsy only has a 40–50% sensitivity in the diagnosis of malignant disease; a critical shortcoming.

There are two approaches to percutaneous needle biopsy: core biopsy and needle aspiration. In core biopsy the needle is advanced into tissue for obtaining a core or plug of tissue sample within the interior of the needle which is subsequently withdrawn. In needle aspiration tissue is obtained by inserting the needle to the desired tissue site and applying a vacuum to suck cells and tissue through the needle and outside the body. Each of these procedures has its respective tradeoffs and limitations. However, both still present a significant risk of pneumothorax, particularly with increasing needle path length through the lung (R. Erlemann: "Punch biopsy or fine needle aspiration biopsy in percutaneous lung puncture." Radiologe. 1998 February;38(2):126–34.).

While the core biopsy approach has been able to obtain larger tissue samples that provide increased diagnostic accuracy and sensitivity verses fine needle aspiration, it has the disadvantage of a higher incidence of complications including pneumothorax. This is in part due to the fact that currently available core biopsy needles (e.g. Silverman, Cope and Abrams) are likely to cause sizable injury to the pleural surface of the lung, a condition which promotes pneumothorax. Specifically, the rigidity of such needles against the lung tissue results in tearing or stretching of the tissue at the point of entry, such that leakage may occur while the needle is in place. Further, these needles do not include an air seal, resulting in an increased chance of air being introduced from outside the body (through the needle) also causing the lung to collapse and or an air embolism (discussed herein).

Also, larger diameter biopsy needles such as those used in core biopsy have an increased risk of puncturing a pulmonary vessel resulting in uncontrollable bleeding. The risk of vessel perforation results from the fact that the physician is at times without visualization from flouroscopy or a viewing device being effectively blind as to the position of the biopsy needle within the lung. Once a vessel is punctured, uncontrollable bleeding can quickly result as an well as air embolism. The extent of vessel damage and resultant bleeding is related to the diameter of the biopsy needle and the shape of the tip.

Air embolism is another complication of percutaneous lung biopsy. Embolism occurs when the needle enters a vessel in the lung and when the biopsy needle or stylet is removed to apply negative suction. Air sucked into the vessel in this manner may markedly decrease the pressure in the vessel. When air gets into the vessel it travels to vital organs and blocks the blood supply and the patient can die as a result.

Currently, the only satisfactory percutaneous lung biopsy procedure from a safety standpoint is the "Skinny Needle" technique. In this procedure a needle, similar to a standard intravenous needle (18 to 21 gauge) but somewhat longer and having an angled sharp cutting tip, is attached to a syringe. The needle is inserted into the lung through the chest wall and a vacuum is applied to the syringe whereby lung cells are sucked into the needle. The needle is then withdrawn from the chest and the cells forced from the needle onto a microscope slide for examination. This technique is simple since it can be performed at the patient's bedside; quickly, 15 to 30 minutes, and inexpensively. Since the needle is of narrow bore and has a sharp cutting tip, the injury to the pleural surface is minimal. This, together with the needle being air-sealed by the syringe, results in a lower incidence of lung collapse versus other percutaneous techniques. However the "Skinny Needle" device and technique have a limitation that makes it the least satisfactory of all lung biopsy techniques, that is the relative paucity of tissue obtained due to the structure of the lung being predominantly air. This is a critical shortcoming in that larger tissue sample sizes are preferred or necessary particularly for histological tissue examination since certain diseases can not be diagnosed by other methods (e.g. cytologically). In many instances, the larger tissue sample sizes required by histological examination has required open lung biopsy procedures.

Thus, the currently available percutaneous lung biopsy needles face a design trade off in terms off efficacy versus safety. They need to strike a balance between needle diameter, flexibility and stiffness to minimize the chance pneumothorax and improve the sample size. Unfortunately, none have succeeded and all have had to comprise safety or diagnostic accuracy to some extent. Additionally none of the currently available lung biopsy needles address various contraindications in doing a biopsy. These include: (i) absence of sufficient pleural fluid, making it difficult to recognize the plane of cleavage of visceral and parietal pleura resulting in a high likelihood of lung perforation/pneumothorax; (ii) empyema; (iii) uremia; (iv) use of mechanical ventilation devices; hemothorax, which is accidental injury to the neurovascular bundle; resulting from misdirection of the biopsy hook upward along the inferior margin of the rib; and (v) coagulation defect, resulting in a likelihood of pleural bleeding.

Clearly, there is a need for a lung biopsy device and procedure that is able to satisfy previously unmet safety and efficacy requirements. These include being able to obtain a sufficient biopsy tissue sample to make reliable diagnosis from an organ that is mostly air without causing pneumothorax, embolism, hemorrhage, pleural trauma or other injury or adverse complication. There is also a need for a device and procedure that allows the physician to monitor for air leakage into the lung and pleural space to prevent pneumothorax before it happens. There is also a need for a device and procedure that allows the physician to reliably seal tears within the pulmonary and pleural tissue to prevent pneumothorax or plumonary hemorrhage. There is a further need for a device that can be precisely positioned in a target tissue zone. Yet another need exists for a lung treatment apparatus that can controllably and completely ablate a lung selectable lung tissue volume.

SUMMARY OF THE INVENTION

An embodiment of a lung treatment apparatus includes an elongated member having a proximal portion, a distal portion and a lumen. The distal portion includes a tissue piercing distal end having at least one of a flexibility, a lubricity or a shape configured to minimize injury to a pleural membrane. An energy delivery device is coupled to the distal portion of the elongated member. The energy delivery device has a shape configured to deliver energy to a target lung tissue volume including sufficient energy to close a void space within or adjacent the tissue volume. The energy delivery device is further configured to be coupled to a power source. At least one aperture is coupled to one of the elongated member or the energy delivery device. A sensor is coupled to the elongated member.

In another embodiment, a lung treatment apparatus includes an elongated member having a proximal portion, a distal portion, a lumen and at least one aperture coupled to the lumen. The distal portion includes a tissue piercing distal end configured to minimize injury to a pleural membrane. An energy delivery device is coupled to the distal end of the elongated member. The energy delivery device has a shape configured to deliver energy to a target lung tissue volume. The energy delivery device is further configured to be coupled to a power source. A closure device is coupled to the elongated member. The closure device is configured to substantially close a tissue void space within the lung.

In yet another embodiment, a lung treatment apparatus has an energy delivery device that includes a first RF electrode with a tissue piercing distal portion and a second RF electrode with a tissue piercing distal portion. The first and second RF electrodes are positionable in the introducer as the introducer is advanced through tissue and deployable with curvature from the introducer at a selected tissue site. A groundpad electrode is coupled to the first and second RF electrodes. A first sensor is coupled to the groundpad electrode.

In another embodiment, a method of ablating a selected pulmonary tissue mass is provided utilizing a multiple antenna device with feedback control. The multiple antenna device can be an RF antenna, a microwave antenna, a short wave antenna and the like. At least two secondary antennas can be included and laterally deployed from the primary antenna. The secondary antenna is retractable into the primary antenna, permitting repositioning of the primary antenna. When the multiple antenna is an RF antenna, it can be operated in monopolar or bipolar modes, and is capable of switching between the two. One or more sensors are positioned at an interior or exterior of the primary or secondary antennas to detect impedance or temperature. The feedback control system is coupled to each of the sensors and to the primary antenna which delivers RF, microwave, short wave energy and the like from the energy source to the secondary antennas while delivering electromagnetic energy to a targeted tissue mass. A cable connects the primary antenna to the energy source. One or more of the secondary antennas are electromagnetically coupled to the primary antenna to receive ablation energy from the primary antenna. Although the primary antenna is an antenna it need not have an ablation energy delivery surface. An insulation sleeve can be positioned around the primary and secondary antennas. Another sensor is positioned at the distal end of the insulation sleeve surrounding the primary antenna. The feedback control device can detect impedance or temperature at a sensor. In some embodiments, the feedback control system can include a multiplexer. Further, the feedback control system can provide an ablation energy output for a selected length of time, adjust ablation energy output and reduce or cut off the delivery of the ablation energy output to the antennas. The feedback control system can include a temperature detection circuit which provides a control signal representative of temperature or impedance detected at any of the sensors. Further, the multiple antenna device can be a multi-modality apparatus. One or all of the antennas can be hollow to receive an infusion medium from an infusion source and introduce the infusion medium into the targeted tissue mass.

Embodiments of the invention provide the advantage of being able to employ minimally invasive methods to rapidly obtain sufficient biopsy tissue samples to make accurate diagnosis of pulmonary disease while significantly reducing the risk of pneumothorax. Embodiments of the invention also provide the advantage of allowing the physician to obtain adequate biopsy tissue samples using an atraumatic device and method that reduces the risk of trauma including tears to pulmonary and pleural tissue, hemothorax and pulmonary hemorrhage and embolism. The invention further provides the advantage of an apparatus that prevents air from being accidentally sucked into the lung through the use of a control valve and can reliably seal perforated lung tissue at the biopsy site so as to prevent a pneumothorax or uncontrolled hemorrhage. Still further, the invention provides the advantage of using minimally invasive methods to treat a selected pulmonary tissue volume to achieve a desired treatment endpoint including complete ablation/ necrosis of the selected tissue with minimal effect on surrounding tissue.

BRIEF DESCRIPTION OF THE FIGURES

FIGS. 9a–9h are lateral views illustrating various configurations of the electrode including ring-like, ball, hemispherical, cylindrical, conical and needle-like.

FIGS. 22a and 22b are lateral views illustrating embodiments using coiled springs and tapered springs as a closure device.

DETAILED DESCRIPTION

Figure 1:
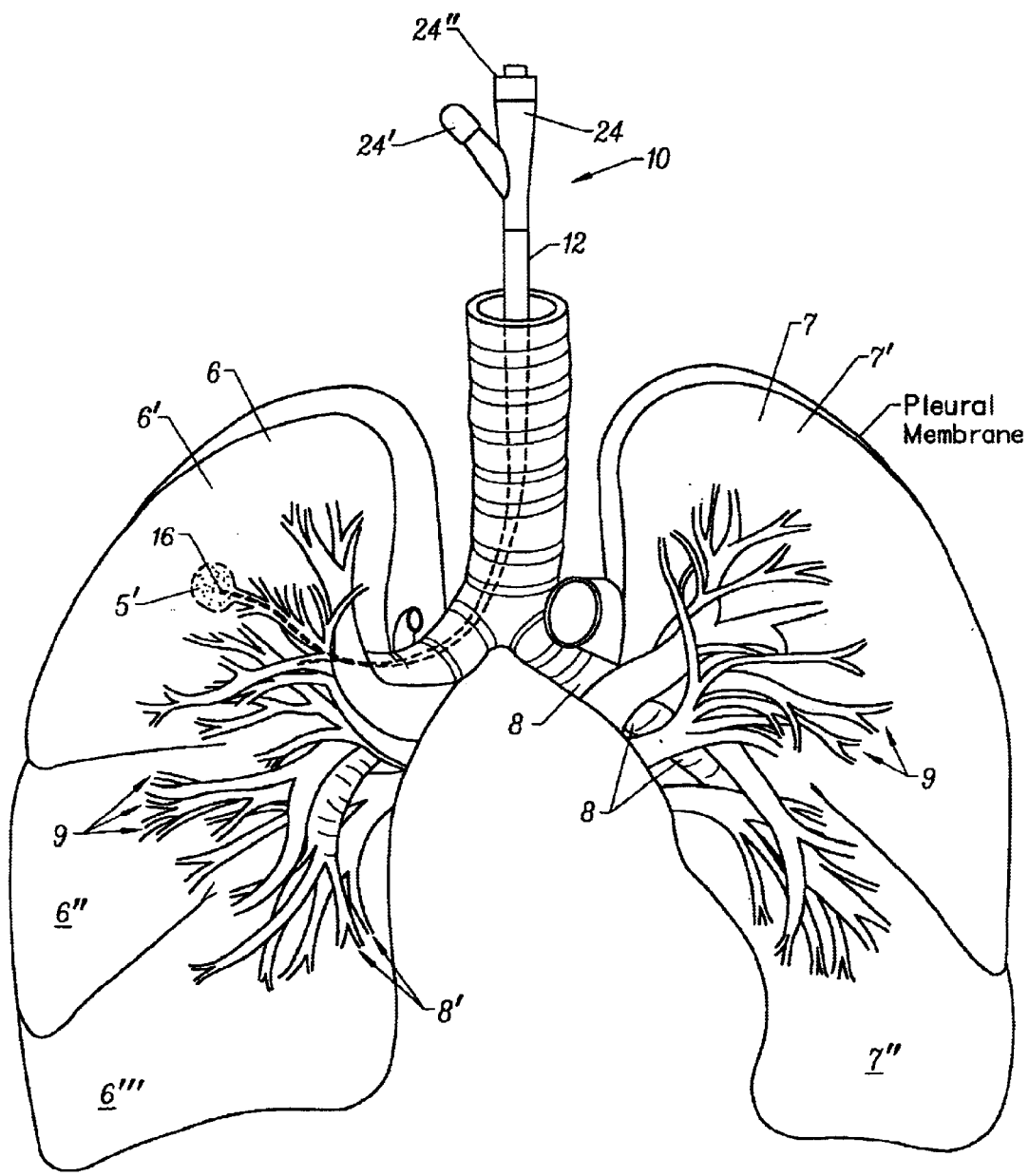
FIG. 1 is a perspective view of the pulmonary anatomy and also shows positioning of an embodiment of a lung treatment apparatus.

FIG. 1 depicts the placement of lung treatment apparatus 10 in lung 5 to treat a target tissue site. To facilitate an understanding of the use of various embodiments of apparatus 10 a discussion of lung anatomy will now be presented. Each lung has four surfaces: i) Apex, ii) Base, iii) Costovertebral iv 4) Mediastinal/Hilum. The right lung 6 is slightly larger than the left lung and has three lobes: upper 6'; middle 6"; and lower 6'". These lobes are divided by the oblique and horizontal fissures. The left lung 7 only has two lobes, an upper 7' and lower 7'". These lobes are divided by the oblique fissure. Both lungs 5 are further divided by bronchopulmonary segments or bronchi 8 that narrow down to bronchioles 8'. The lung is vascularized with a variety of pulmonary vessels 9, including pulmonary arteries, veins and capillaries.

In an embodiment, lung treatment apparatus 10 is configured to be positioned in any anatomical portion of either lung including individual bronchioles 8' to image, sample or treat lung tissue at tissue site 5'. Tissue site 5' can be located in any location in the lung 5 (e.g. lobe, fissure, bronchial or pulmonary vessel) and can include lesions, tumor sites, disease/infected site, edemic site, embolism, clots, tears, trauma sites and the like. Once positioned at target tissue site 5', apparatus 10 can be configured to treat tissue at that site as well as collect a tissue sample using a biopsy device disclosed herein.

Figure 2:
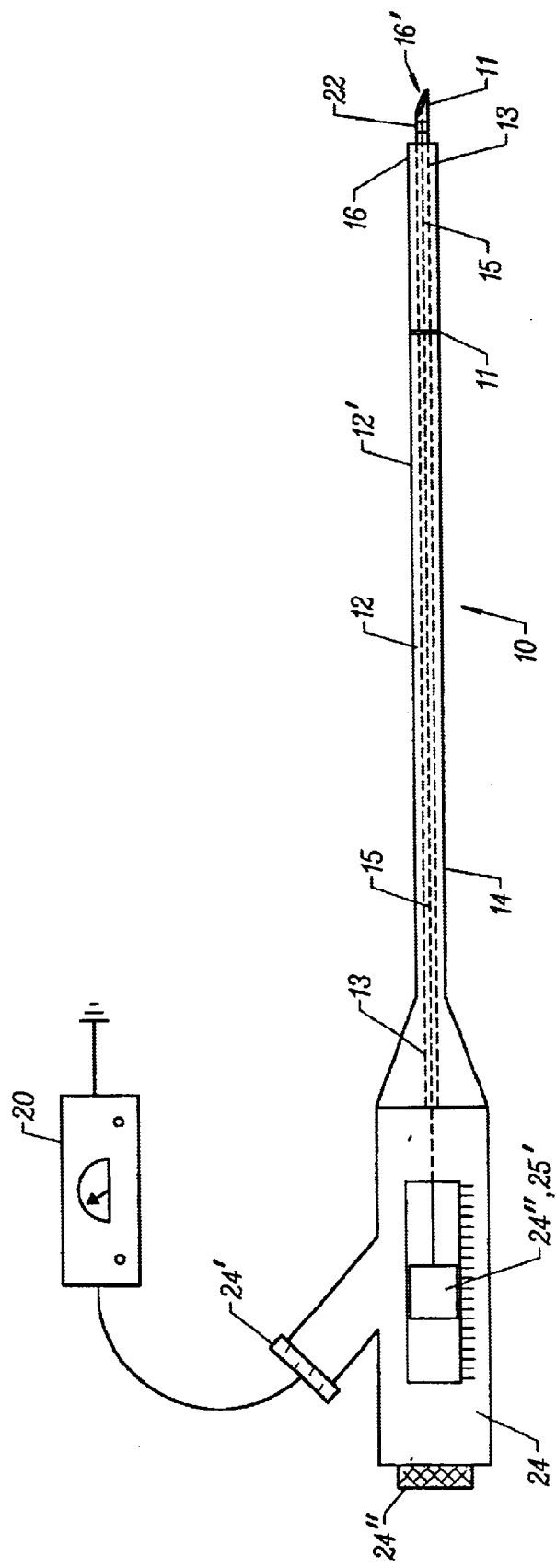
FIG. 2 is a lateral view of an embodiment of the lung treatment apparatus illustrating components of the apparatus including the elongated member, energy delivery device and biopsy needle.

Referring now to FIG. 2, an embodiment of a lung biopsy apparatus 10 includes an elongated member or shaft 12 with a proximal end 14 and a distal end 16'. Distal end 16 may be sufficiently sharp to penetrate tissue including muscle, cartilage and bone. Shaft 12 may have one or more lumens 13 that may extend over all or a portion of its length. An energy delivery device, generally denoted as 18, is coupled to distal end 16'. Energy delivery device 18 is configured to be coupled to an energy or power source 20. A sensor 22 may be coupled to shaft 12 including distal end 16' and energy delivery device 18.

Figure 3A:
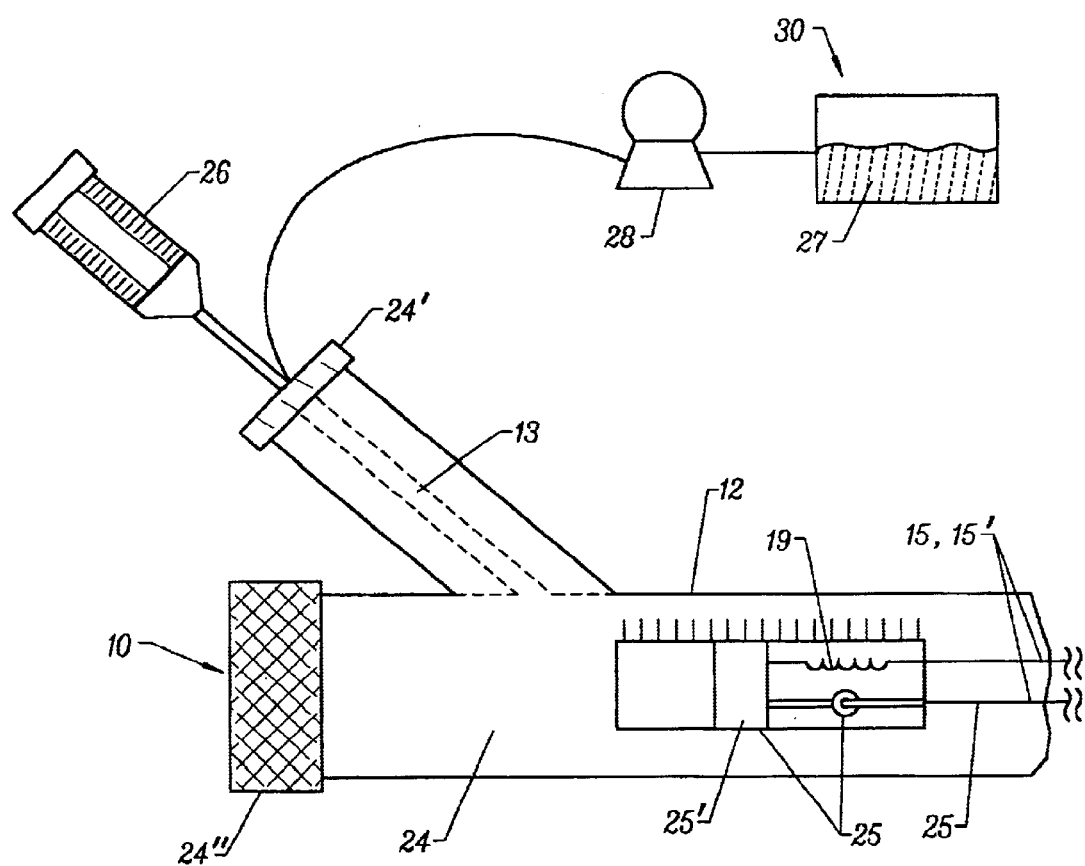
FIG. 3a is a lateral view illustrating components of the handpiece and deflection mechanism.
Figure 3B:
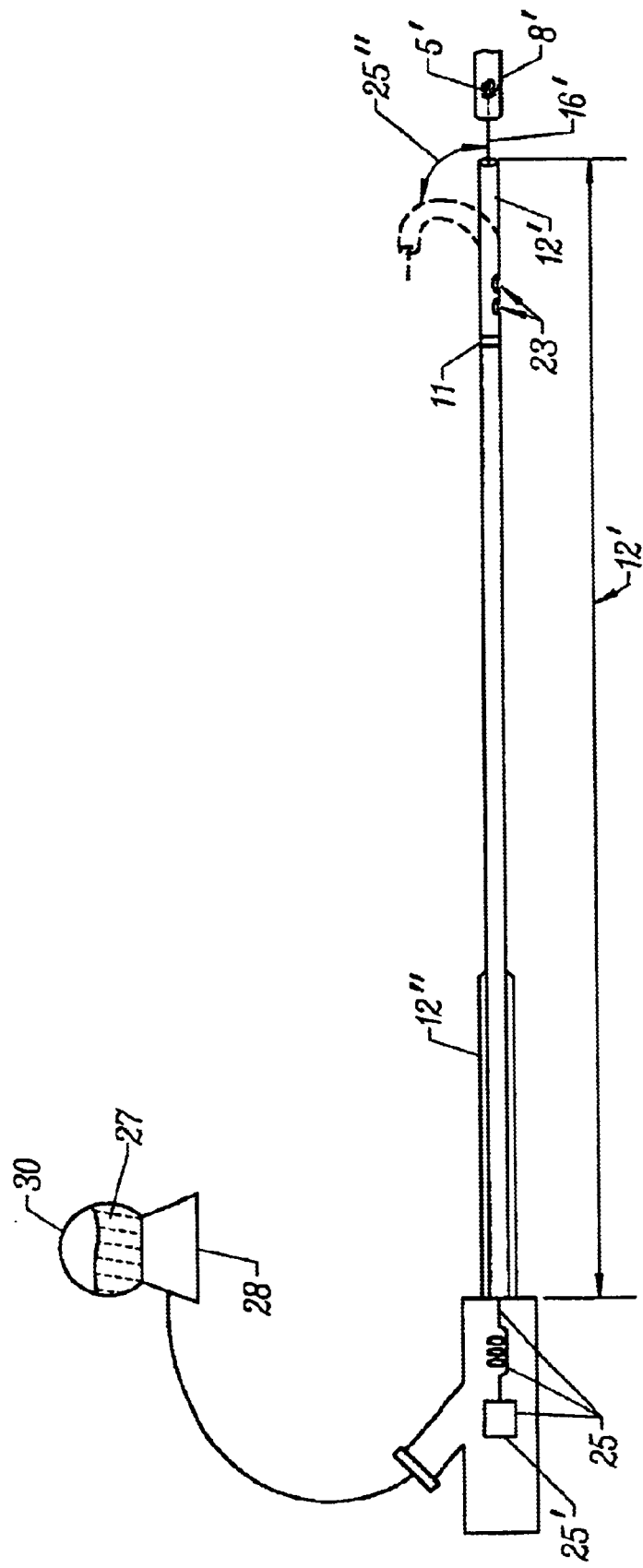
FIG. 3b is a lateral view illustrating use of the handpiece and deflection mechanism.

For ease of discussion, shaft 12 will now be referred to as an introducer 12 but all other embodiments discussed herein are equally applicable. Referring now to FIGS. 2, 3a and 3b, in various embodiments, introducer 12 can also be coupled at its proximal end 14 to handle 24. Handpiece 24 can be detachable and can include ports 24' and actuators 24". Ports 24' can be coupled to one or more lumens 13 and can include fluid and gas ports/connectors and electrical, optical connectors. In various embodiments, ports 24' can be configured for aspiration (including the aspiration of tissue), and the delivery of cooling, electrolytic, irrigation, polymer and other fluids (both liquid and gas) described herein. Ports 24' can include but are not limited to luer fittings, valves (one-way, two-way), toughy-bourst connectors, swage fittings and other adaptors and medical fittings known in the art. Ports 24' can also include lemo-connectors, computer connectors (serial, parallel, DIN, etc) micro connectors and other electrical varieties well known to those skilled in the art. Further, ports 24' can include opto-electronic connections which allow optical and electronic coupling of optical fibers and/or viewing scopes to illuminating sources, eye pieces, video monitors and the like. Actuators 24' can include rocker switches, pivot bars, buttons, knobs, ratchets, levers, slides and other mechanical actuators known in the art, all or portion of which can be indexed. These actuators can be configured to be mechanically, electro-mechanically, or optically coupled to pull wires, deflection mechanisms and the like allowing selective control and steering of introducer 12. Handpiece 24 can be coupled to tissue aspiration/collection devices 26, fluid delivery devices 28 (e.g. infusion pumps) fluid reservoirs (cooling, electrolytic, irrigation etc) 30 or power source 20 through the use of ports 24'. Tissue aspiration/collection devices 26 can include syringes, vacuum sources coupled to a filter or collection chamber/bag. Fluid delivery device 28 can include medical infusion pumps, Harvard pumps, syringes and the like. In specific embodiments, aspiration device 26 can be configured for performing thoracentesis which is a procedure for removing pleural fluid percutaneously.

In various embodiments, at least portions of lung treatment apparatus 10 including introducer 12 and distal end 16' may be sufficiently radiopaque to be visible under fluoroscopy and the like and/or sufficiently echogenic to be visible using ultrasonography. In specific embodiments, introducer 12 can include radiopaque or echogenic markers 11, at selected locations including along all or portions of introducer 12 including distal end 16'. Markers 11 can be disposed along introducer 12 to facilitate identification and location of tissue penetrating portion 16 including tissue collection portions, ports, sensors as well as other components and sections of lung treatment apparatus 10 described herein. In an embodiment, markers 11 can be ultrasound emitters known in the art. Also treatment apparatus 10 can include imaging capability including, but not limited to, fiber optics, viewing scopes such as a bronchoscope, an expanded eyepiece, video imaging devices, ultrasound imaging devices and the like.

In various embodiments, apparatus 10 can be configured to be introduced into the lung trans-orally through a bronchioscope and the like or percutaneously through the chest wall or nearby tissue with or without the aid of a second introducer discussed herein. For either approach, apparatus 10 can be introduced with the aid of a guidewire 15 which introducer 12 is configured to track over. Guidewire 15 can be any of a variety of flexible and/or steerable guide wires or hyptubes known in the art. Introducer 12 can have sufficient length to position distal tip 16' in any portion or lobe of the lung 5 using either a percutaneous or a bronchial/transoral approach. The length of introducer 12 can range from 5 to 180 cms with specific embodiments of 20, 40, 80, 100, 120 and 140 cms. A preferred range includes 25 to 60 cms. The length and other dimensional aspects of introducer 12 can also be configured for pediatric applications with a preferred range in these embodiments of 15 to 40 cms. The diameter of introducer 12 can range from 0.020 to 0.5 inches with specific embodiments of 0.05, 0.1 and 0.3 inches as well as 1, 3, 6, 8 and 10 french sizes as is known in the art. Again, the diameter can be configured for pediatric applications with pediatric sizes of 1, 3 and 6 french. In various embodiments the diameter of distal end 16 can range from 0.010 to 0.1 inches, with specific embodiments of 0.020, 0.030 and 0.040 inches. The diameter of distal end 16' can be configured to be positioned in individual bronchioles 8' such embodiment includes diameters of 0.40" or smaller.

In various embodiments, introducer 12 can be flexible, articulated and steerable and can contain fiber optics (including illumination and imaging fibers), fluid and gas paths, and sensor and electronic cabling. Introducer 12 is sufficiently flexible to pierce tissue, and move in any desired direction through tissue to tissue site 5'. In another embodiment, introducer 12 is sufficiently flexible to reverse its direction of travel and move in direction back upon itself. In specific embodiments, introducer 12 can be a catheter, multi-lumen catheter, or a wire-reinforced or metal-braided polymer shaft, trocar, port device (such as those made by the Heartport® Corp., Redwood City, Calif.), subcutaneous port or other medical introducing device known to those skilled in the art. Also introducer 12 can have a substantially circular, semicircular, oval or crescent shaped cross section, as well as combinations thereof along its lengths. Similarly, lumens 13 can have a circular, semicircular, oval or crescent shaped cross section for all or a portion of the length 12" of introducer 12.

Referring now to FIGS. 3a and 3b, in other embodiments all or portions of introducer 12 can be configured to be deflectable and/or steerable using deflection mechanisms 25 which can include pull wires, ratchets, latch and lock mechanisms, piezoelectric materials and other deflection means known in the art. The amount of deflection of introducer 12 is selectable and can be configured to allow the maneuvering of introducer 12 through very tortuous and/or obtuse pulmonary anatomy including bronchioles 8' and pulmonary vessels 9. In specific embodiments, the distal portions of introducer 12 can be configured to deflect 0–180° or more in up to three axises to allow the tip of introducer 12 to have retrograde positioning capability. Deflection mechanism 25 can be coupled to or integral with a moveable or slidable actuator 25' on handpiece 24. Mechanism 25 and coupled actuator 25' are configured to allow the physician to selectively control the amount of deflection 25 of distal tip 16' or other portion of introducer 12. Actuator 25' can be configured to both rotate and deflect distal tip 16 by a combination of rotation and longitudinal movement of the actuator.

Suitable materials for introducer 12 include, but are not limited to, stainless steel, shape memory alloys such as nickel titanium alloys, polyesters, polyethylenes, polyurethanes, Pebax®, polyimides, nylons, copolymers thereof and other medical plastics known to those skilled in the art. All or portions of introducer 12 can be coated with a lubricious coating or film 12' which reduces the friction of introducer 12 with pulmonary and other tissue. Such coatings can include but are not limited to silicones, PTFE (including Teflon®) and other coatings known in the art. Also, all or portions of apparatus 10 include introducer 12 can be constructed of materials known in the art that are optimized and/or compatible with radiation sterilizations (e.g. Gamma or E-beam). In related embodiments all or portions of apparatus 10 can be configured (e.g. lumen diameter to length ratio, etc) by plasma (eg. $H_2O_2$) sterilization by systems such as Sterad® System made by the Johnson & Johnson Corporation.

In various embodiments, introducer 12 can configured to have varying mechanical properties along its length 12" including, but not limited to variable stiffness, torquability, bendability, flexural modulus, pushability, trackability and other introducer and mechanical performance parameters known in the art. This can be achieved through the use of stiff shafts sections 12''' disposed within portions of introducer 12 along its length 12". It can also be accomplished through the use of braids, varying/tapered diameters and different materials (e.g. stiffer materials joined to flexible materials) positioned over portions of introducer 12. Sections 12''' made from different materials can be joined using introducer bonding methods known in the art such as hot melt junctions (with and without capture tubes/collates), adhesive joints, but joints and the like. The joining method can be controlled/selected so as to control the mechanical transition between two sections to a desired gradient (e.g. smooth vs. abrupt). In related embodiments, introducer 12 can be configured to have stiffer proximal portions and more flexible distal portions so as to facilitate one or more of the following (i) introducer steerability and positioning of distal tip 16' at a selectable tissue location within the lung 5 (ii) reduced risk of perforation, abrasion and other trauma to lung tissue resulting in reduced risk of pulmonary bleeding, embolism and pneumothorax. In various embodiments, the transition from the stiffer to the more flexible portion can be configured to be gradual with a linear or curve-linear transition or an abrupt transition.

Figure 4A:
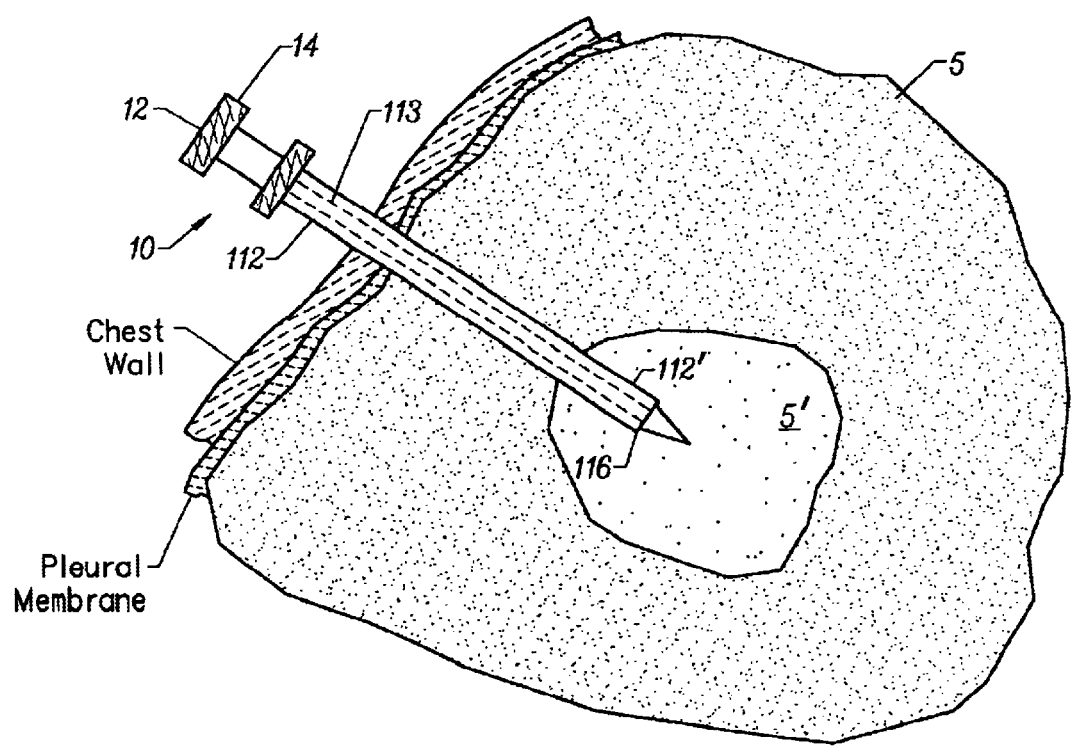
FIGS. 4a and 4b are perspective views illustrating embodiments having a second introducer.
Figure 4B:
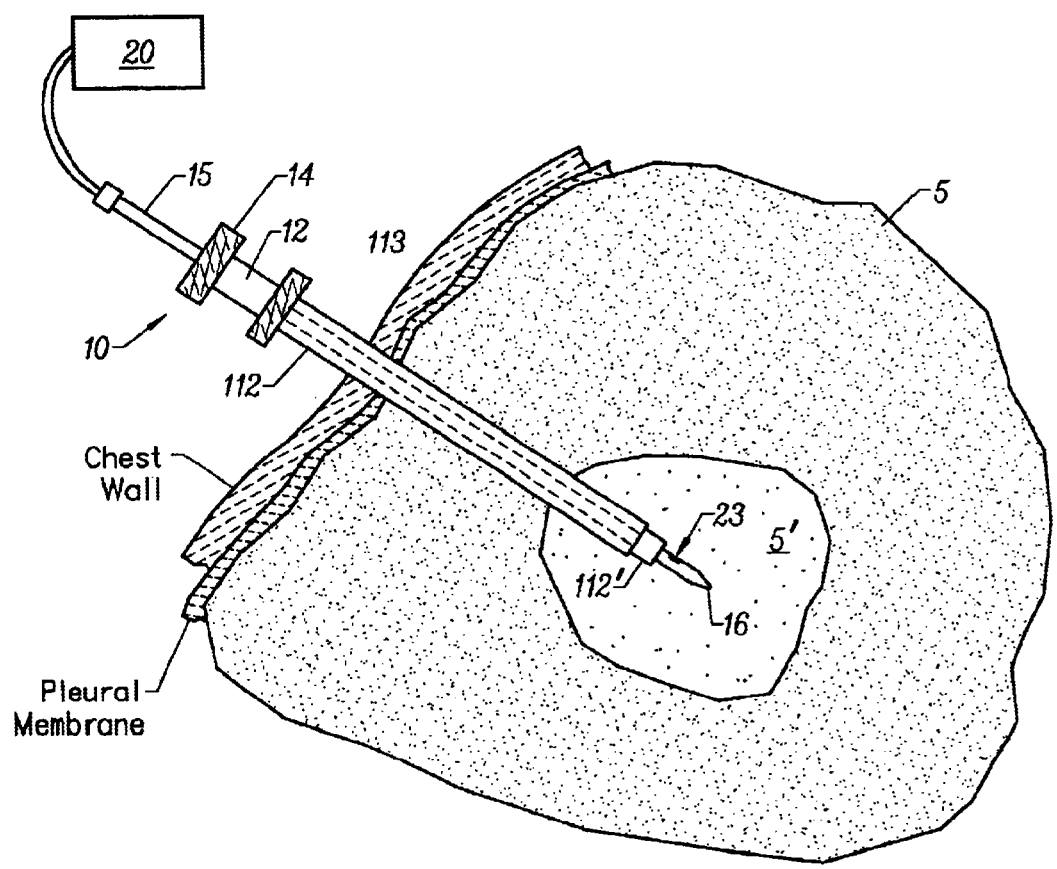

Referring now to FIGS. 4a and 4b, in an embodiment, apparatus 10 can be introduced to the desired tissue site 5' using a second introducer 112. Second introducer 112 can be a conventional sheath which can include a lumen 113 and an obturator/stylet assembly 116 that is introduceable through the skin surface on the chest or through the bronchioscope. In other embodiments, second introducer can be the bronchioscope, a guiding catheter, trocar, port device or other medical introductory devices known in the art.

For ease of discussion, second introducers 112 will now be referred to as sheath 112 but all other discussed embodiments are equally applicable. Sheath 112 can be introduced and positioned such that a distal end 112' of the sheath 112 lies at or within a target tissue site 5'. In various embodiments, introducer 112 and obturator/stylet assembly 116 may be introduced percutaneously directly through the patient's skin over the chest. In other instances it may be desirable to provide an open surgical incision or to place a trocar through the skin in order to introduce the stylet to the tissue site. In either case, the obturator/stylet 116 is then removed from sheath 112, leaving the sheath in place as shown in FIG. 4b. Introducer/shaft 12 of apparatus 10 may then be introduced through the lumen 113 of sheath 112 so that a distal end 16' advances from sheath 112 into the target tissue region 5', also as shown in FIG. 4b.

Figure 5A:
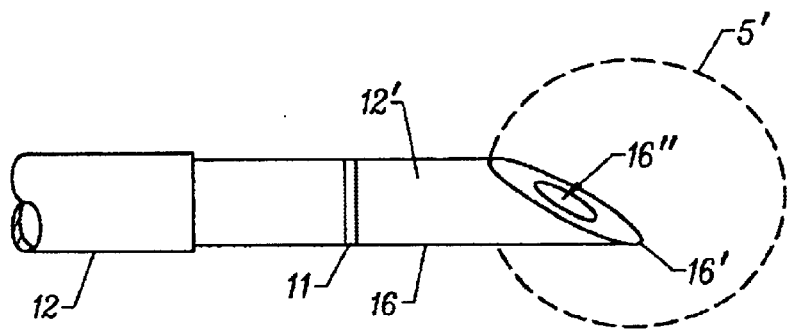
FIG. 5a is a lateral view illustrating an embodiment of the biopsy needle.

Referring now to FIG. 5a, in various embodiments, the distal tip 16' of introducer 12 is sufficiently sharp to penetrate tissue including but not limited to, pulmonary tissue, bone, cartilage, fibrous and/or encapsulated tumor masses. Distal tip 16' can be a needle that is integral or otherwise coupled to introducer 12 by joining means known in the art such as adhesive bonding, soldering, RF welding, crimping and the like. Needle 16 can have a beveled tip 16' or otherwise atraumatic shape configured to reduce trauma and bleeding from introduction to tissue site 5' particularly when the tissue site includes a pulmonary vessel 9. In other embodiments needle 16 including tip 16' can be given atraumatic qualities through the use of flexible materials (e.g. shape memory materials), tapered shape, or the use lubricious coatings (e.g. Teflon®) described herein.

Needle 16 can have a range of diameters ranging from 10 to 24 gauge, with specific embodiments of 12, 14, 16, 18, 20 and 22 gauge. More preferably, needle 16 can be 19 to 20 gauge, still more preferably needle 16 can be 19.5 gauge. Suitable materials for needle 16 include, but are not limited to, stainless steel including 304, 304V and other stainless steels; shaped memory materials (nickel titanium alloys) and high strength medical plastics known in the art (e.g. polycarbonate, etc.). In some applications, all or a portion of needle 16 can be made of nickel titanium alloys NiTi, commercially available from Raychem Corporation, Menlo Park, Calif. Also, all or portions of needle 16 can be configured to deliver RF or other electromagnetic energy to treat target tissue, seal tissue, cure delivered polymer solutions and facilitate atraumatic positioning of needle 16 to the desired tissue site 5'. In various embodiments, needle 16 can be configured to deliver energy to cut and/or coagulate tissue and or blood to lessen the risk of vessel perforation and quickly seal torn lung tissue and perforated blood vessels.

In various embodiments, needle 16 can be fabricated from a composite of metal and polymer to achieve selectable mechanical and/or material properties including flexibility and atraumatic properties. This can involve the use of a polymer and/or lubricous coating 12' over the surface of the needle. A radiopaque or echogenic marker 11 can be integrated, coated, or otherwise positioned on needle 16 for visualization purposes. In an embodiment marker 11 is placed at needle tip 16'.

Figure 5B:
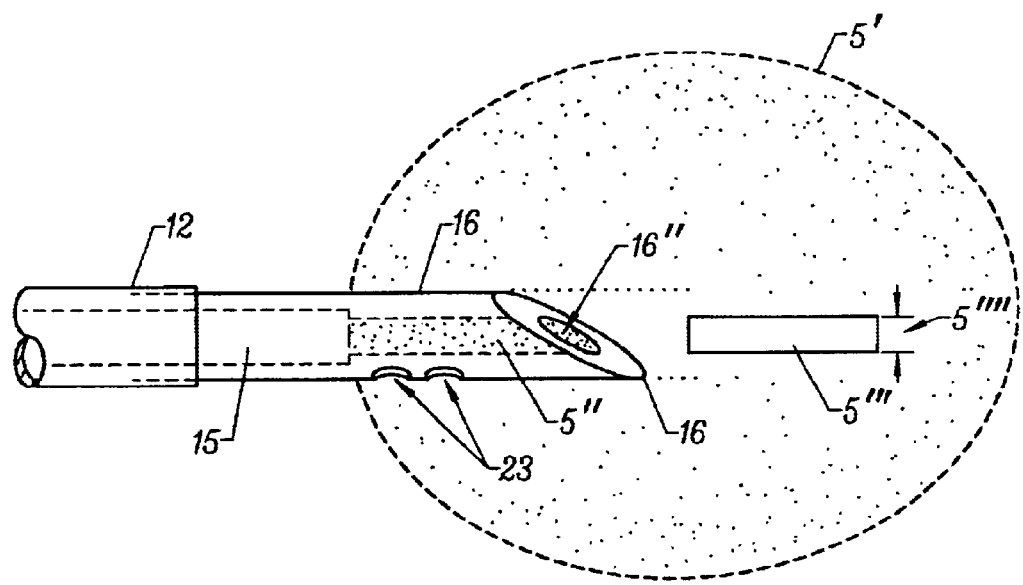
FIG. 5b is a lateral view illustrating use of the biopsy needle to collect a tissue sample.
Figure 5C:
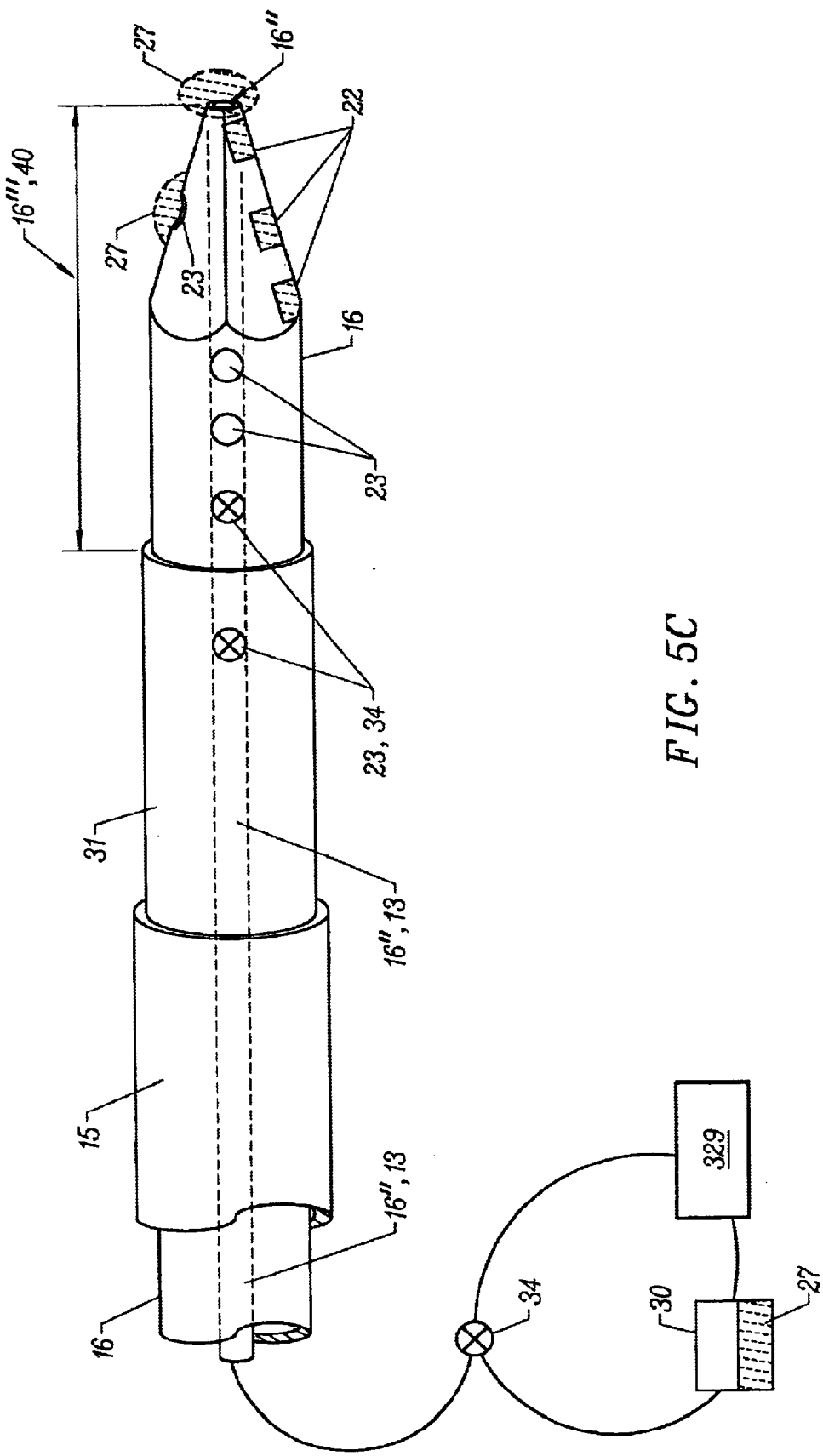
FIG. 5c is a lateral view illustrating an embodiment of the biopsy having an insulative sheath.
Figure 5D:
FIGS. 5d–k are lateral views illustrating various embodiments of the biopsy needle.
Figure 5E:
Figure 5F:
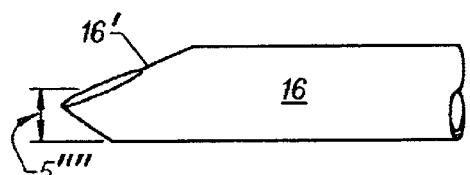
Figure 5G:
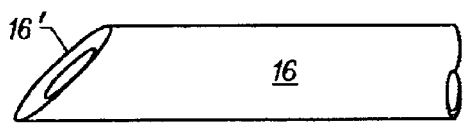
Figure 5H:
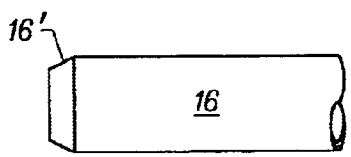
Figure 5I:
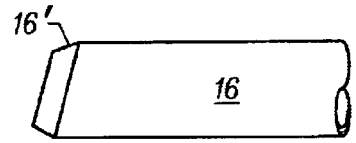
Figure 5J:
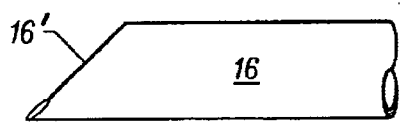
Figure 5K:
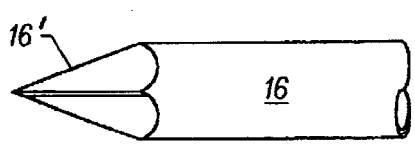

Referring now to FIGS. 5b and 5c, in various embodiments needle 16 can be configured to collect a tissue sample from target tissue site 5'. Accordingly, needle 16 can include at least one lumen 16" for the collection of tissue, delivery of fluids etc. In embodiments, needle 16 can be a core biopsy or aspirating sample needle known in the art. In specific embodiments needle 16 can be a Cope or Abrams type needle or a hypotube of varying diameter. When needle 16 is a core biopsy type needle all or a portion of the length of lumen 16" can be configured to collect a tissue sample 5". The size/length of the biopsy tissue sample collected 5" can be controlled through a variety of means including positioning of guidewire 15 or other wire/mandrel positioned within needle lumen 16" and/or the use of stepped/tapered sections within lumen 16". In various embodiments, the removal of tissue sample 5" may create a tissue void 5'" also called void space 5'" having an area profile 5"". The shape of needle 16 including that of tip 16' can be configured to minimize the size of tissue void 5'" including profile 5"" particularly that in the pleural membrane. In various embodiments shown in FIGS. 5d–5k, this can be accomplished through the use of a shaped needle tip 16' having a minimum cutting profile 5"". Such shaped needle tips 16" can include but are not limited to a beveled tip, a short bevel tip, a long bevel tip, a J-point tip, a V-point tip, an angled conical tip, a trocar tip and other needle tips known in the art. In a preferred embodiment tip 16' is a V-point tip. The use of a shaped needle tip producing a minimal profile 5"" provides the benefit of allowing the elastic pleural tissue in target tissue site 5' to rapidly contract around and close the void space 5'" preventing or otherwise reducing the risk of pneumothrorax.

Needle 16 can also be slidably or reciprocally coupled to introducer 12, either being disposed within introducer 12, or over the outer diameter of introducer 12. Needle 16 can also be detachably coupled to introducer 12 to allow the physician to select the length and diameter needle 16 for the desired tissue biopsy size, tissue location etc. Referring back to FIG. 5c, needle 16 can also have a protective and/or insulative sheath 31 over all a portion of its length that can be slidably advanced over the needle. Sheath 31 can be coupled to introducer 12 and/or wire 15. The amount of exposed needle 16 can be used to select both a cutting depth 40 of needle 16 and a conductive surface area 16'".

Needle 16 can also include one or more sensors 22 disposed on or within needle 16 including within needle 16". Sensors 22 coupled to needle 16 can include pressure and/or flow sensors for sensing air, gas or liquid flow through the needle, or surrounding target tissue site 5' including tissue void space 5'". Pressure and/or flow sensors 22 can be configured to detect very minute pressure differences (e.g. 1 mm Hg or less) and/or flow rates so as to detect leaks before a pneumothorax develops. In another embodiments sensor 22 can be configured to detect the presence of a volume of void space 5'" created by the collection of sample 5" or other event. In these and related embodiments, sensor 22 can be an optical sensor or an ultrasound sensor or transducer either of which can be configured to provide an image of void space 5'" or otherwise detect its presence thorugh differentiation of tissue properties created by the void space (e.g. optical or acoustical density and the like). Needle 16 can also include or be coupled to a control valve 32 (including a one way valve) which prevents air and other fluid from being withdrawn or injected into the needle 16, and/or introducer 12 unless the valve is engaged or a pressure threshold is exceeded. In use, control valve 32 provides the advantage of preventing a pneumothorax by preventing the accidental flow of air into the lung or pleural cavity while needle 16 is being positioned at the treatment site 5', is being exchanged, cuts or collects a sample of tissue or is used to deliver energy. Control valve 32 also prevents air from being sucked into the lung during exchange of a needle stylet or introducer.

Figure 6A:
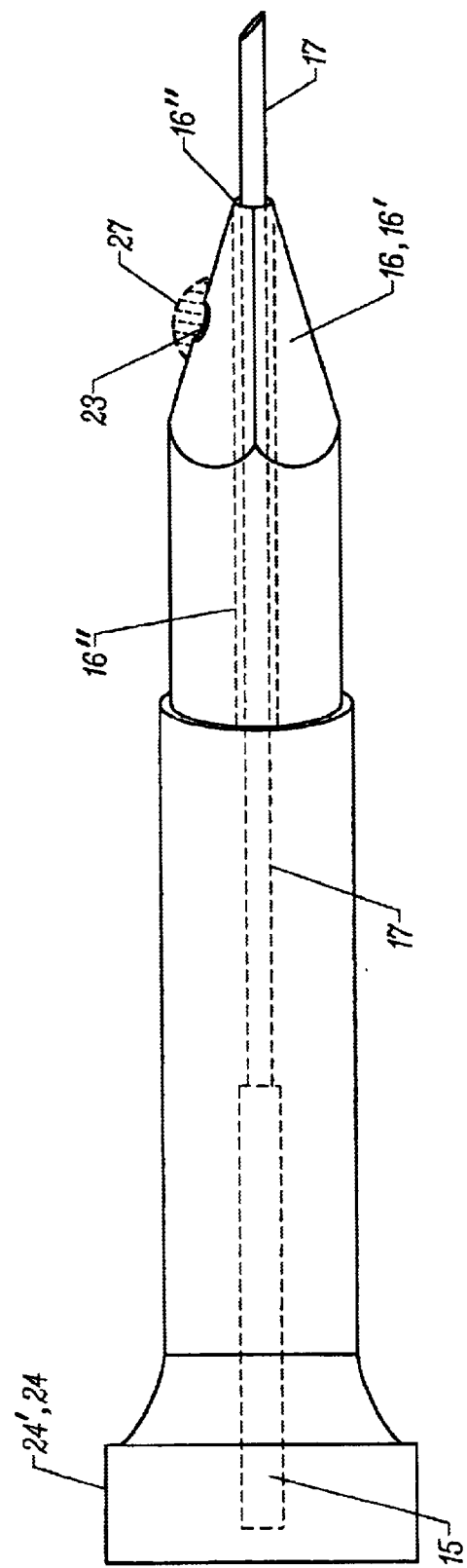
FIG. 6a is a lateral view illustrating an embodiment having a first needle and second biopsy needle/device.
Figure 6B:
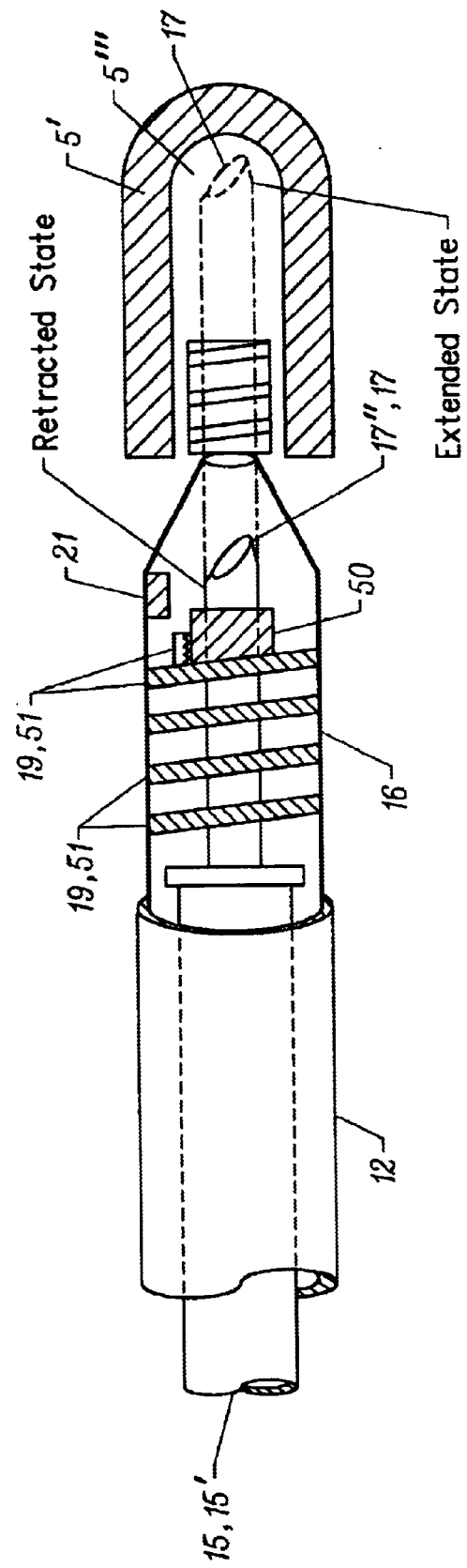
FIG. 6b is a lateral view illustrating an embodiment of FIG. 6a having a spring coupled to the first needle or second biopsy needle/device.

Referring now to FIGS. 6a and 6b, in various embodiments, needle 16 can be adapted to couple to or allow the advancement of a second biopsy device 17, needle and the like. Needle 17 can be positioned within needle 16, including lumen 16". In specific embodiments needle 16 can be configured to allow the advancement of a transbronchial brush biopsy instrument or a core biopsy needle, a Cope type needle or an Abrams type needle, any of which can be slidably mounted within needle 16. Biopsy device 17 can be advanced using a pull or guidewire 15 coupled to device 17 or needle 16. In these and related embodiments, the wire 15 can be freely moving or coupled to a slidable actuator 24" on handpiece 24. Actuator 24" can be indexed and/or spring loaded in order to precisely control and/or limit the lateral advancement and penetration depth of needle 16 or biopsy needle 17.

Referring now to FIG. 6b, biopsy device 17 can also be reciprocally coupled to needle 16 via a spring 19 positioned within needle 16 and/or over biopsy device 17. Spring 19 can have a sufficient spring force (e.g. spring constant) and/or length to control and/or give the physician tactile feedback on the advancement of biopsy device 17 or needle 16. In use, spring 19 (or another spring) can also be mechanically coupled to closure device 50 (described herein) to deploy the closure device at a selected point during the advancement or retraction of device 17 or needle 16. Spring 19 can be coil or leaf spring as is known in the art and can be made from spring steel, 304 or stainless steel known in the art.

In a preferred embodiment, spring 19 is mechanically coupled to the closure device 50, by deployment mechanism 51 (which can be spring, ratchet or cam-based) to deploy the closure device as device 17 is withdrawn back into needle 16 so as to fill, close and/or seal any resulting void space 5''', tear or injury caused by the collection of the tissue sample at or near target tissue site 5'. The advancement of device 17 can also be controlled or limited through the use of a mechanical stop 21 coupled to device 17, needle 16 or both as well as the use of tapered sections 17''' within device 17.

Figure 7:
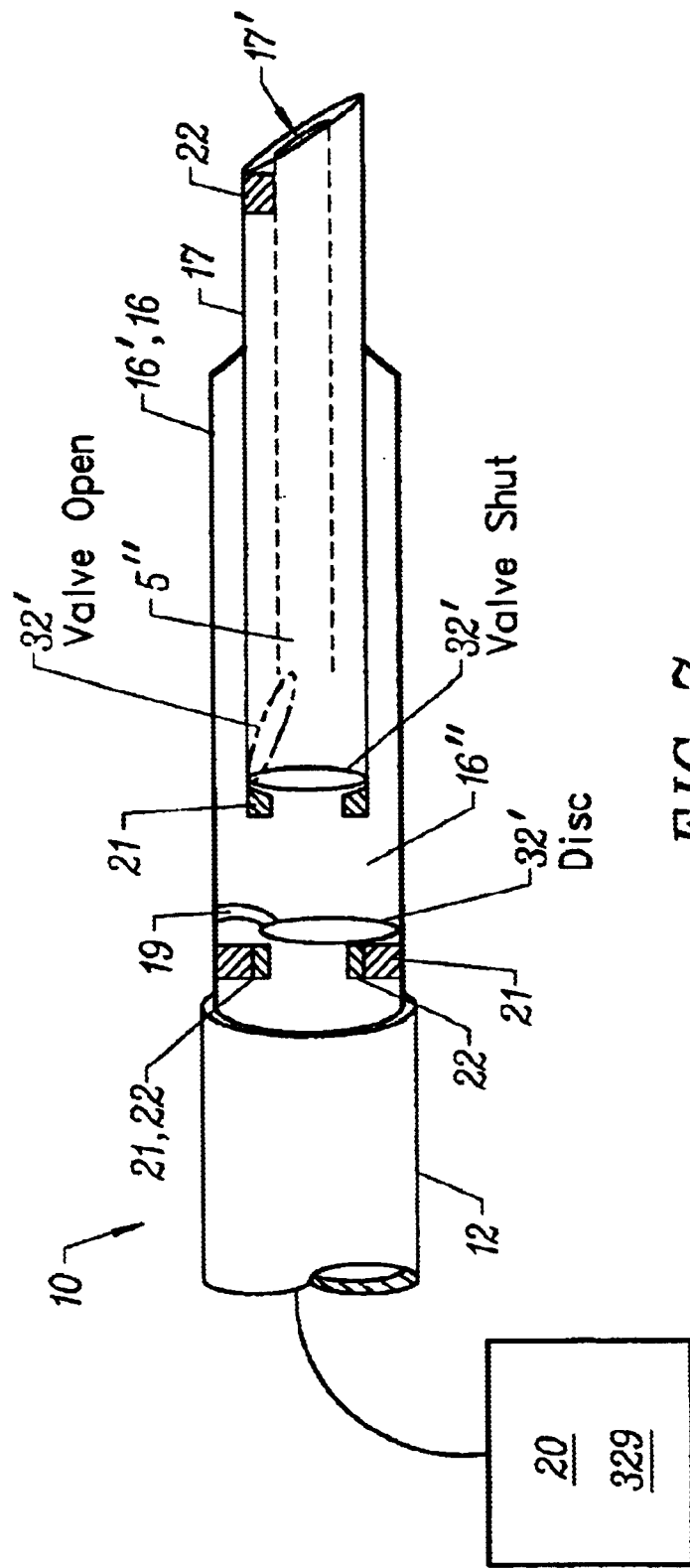
FIG. 7 is a lateral view illustrating an embodiment having disc control valve.

Referring now to FIG. 7, in an embodiment, control valve 32 can be a disc 32' disposed within needle 16 or device 17. Disc 32' can be moved slidably and/or reciprocally positioned within lumens of needle 16 or needle/device 17. Disc 32' can also be pivotally or hingeably attached within either needle and can be configured to pivot either proximally or distally within needle 16 or 17. Disc 32' can be configured to slide proximally within lumen 16" or 17' as either needle is advanced into target tissue 5' to collect a tissue sample 5". Once the tissue sample 5" is collected, disc 32' pivots proximally, allowing tissue sample 5" to be removed through aspiration, mechanical or other means and can then rapidly pivot back distally to close and provide a pressure seal. The bi-directional pivot capability of disc 32' can be achieved through the use of a spring latch or other mechanical means known in the art.

Figure 8:
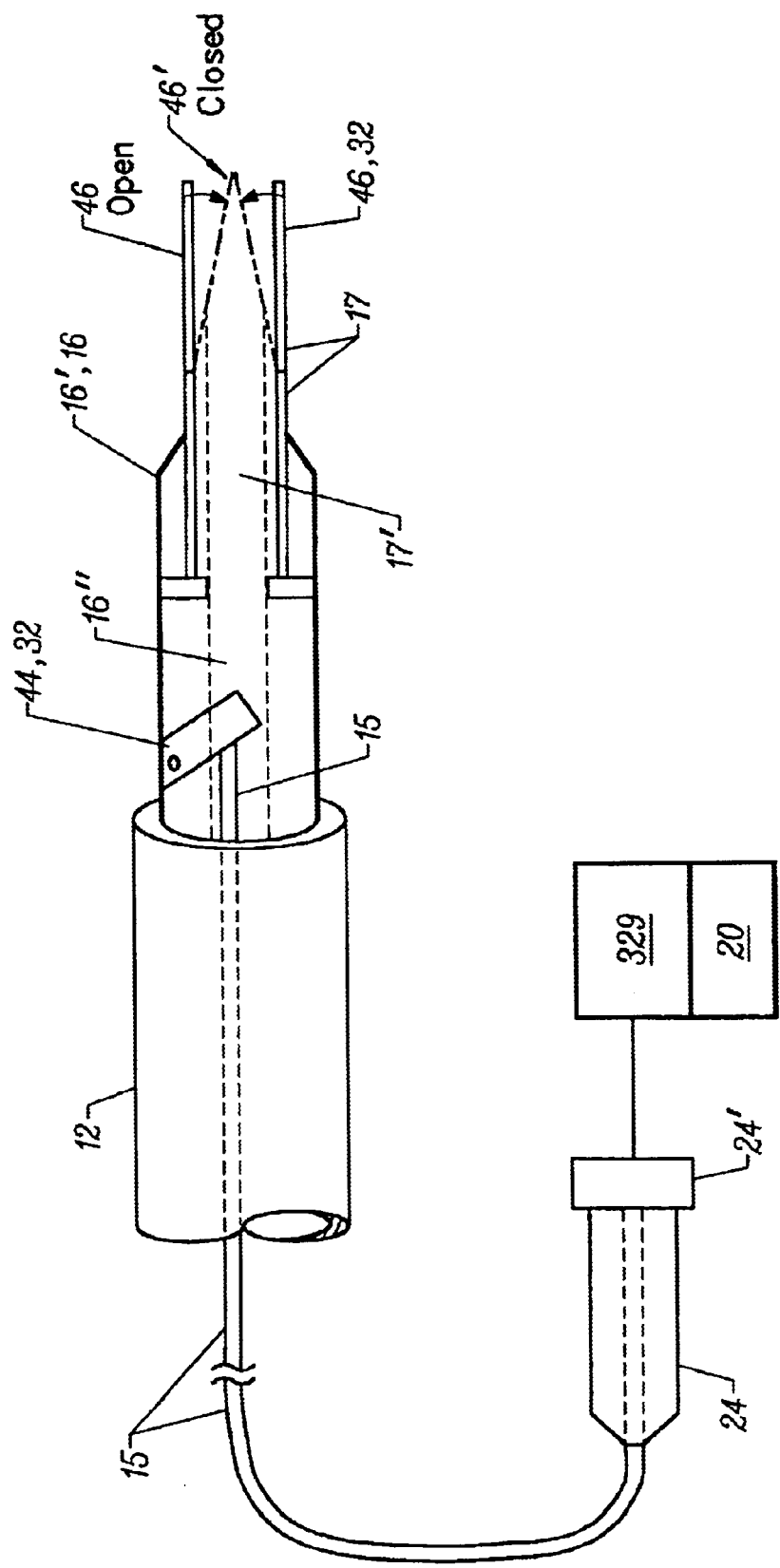
FIG. 8 is a lateral view illustrating an embodiment having a constrictable control valve.
Figure 9A:
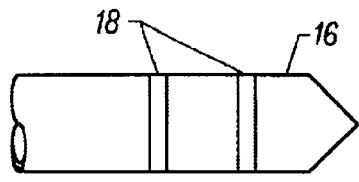
Figure 9B:
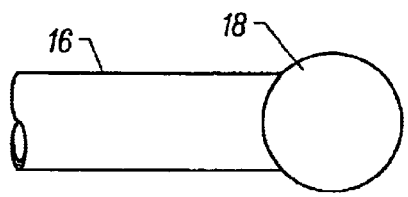
Figure 9C:
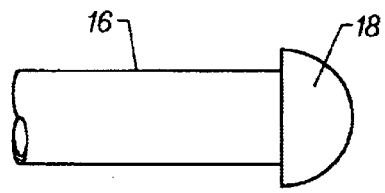
Figure 9D:
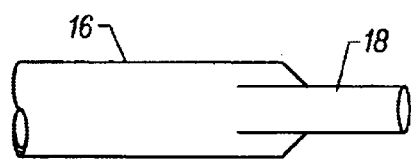
Figure 9E:
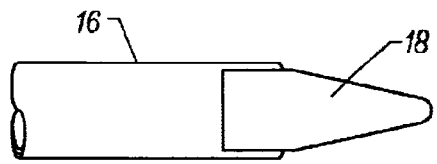
Figure 9F:
Figure 9G:
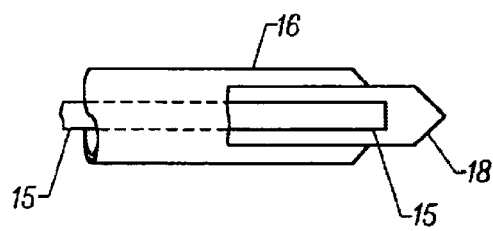
Figure 9H:
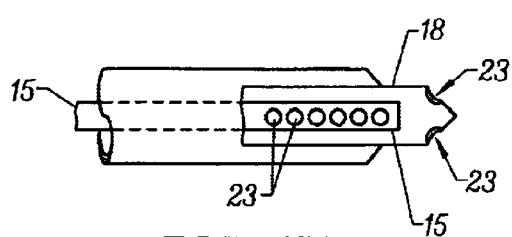

Referring now to FIG. 8, in other embodiments, control valve 32 can comprise a constrictable portion 44 of needle 16 or needle 17. Constrictable portion 44 can be located at any point along the length of needle 16 or needle, but is preferably positioned near their respective distal ends. In use, constrictable portion 44 is configured to allow the lumens of needle 16 or 17 to be constricted sufficiently to prevent the flow of fluid including gas to prevent a pneumothorax. Constrictable portion 44 can be actuated automatically (via control system 329 discussed herein) or manually before, during or after the collection of a tissue sample. Constrictable portion 44 can comprise a clamp or other closure device actuable from handpiece 24 via a pullwire 15 or other means. In a related embodiment constrictable portion 44 can comprise a section of shaped memory material 46 which is given a memory/set of a smaller diameter/contracted shape 46' via heat treatment (known in the art) such that upon an increase in temperature from a heated fluid or delivery of RF energy, shaped memory section 46 assumes a contracted/constricted state/shape 46' sufficient to constrict needles 16, 17 as described herein. In related embodiments, constrictable portion 44 can be fabricated from piezoelectric materials which can be controllably constricted through the use of an electric current/signle which can be controlled by the use of control system 329 described herein.

A variety of energy delivery devices and power sources can be utilized by the invention. Specific energy delivery devices 18 and power sources 20 that can be employed in one or more embodiments include but are not limited to, the following: (i) a microwave power source coupled to a microwave antenna providing microwave energy in the frequency range from about 915 MHz to about 2.45 GHz (ii) a radio-frequency (RF) power source coupled to an RF electrode, (iii) a coherent light source coupled to an optical fiber or light pipe, (iv) an incoherent light source coupled to an optical fiber, (v) a heated fluid coupled to a catheter with a closed or at least partially open lumen configured to receive the heated fluid, (vi) a cooled fluid coupled to a catheter with a closed or at least partially open lumen configured to receive the cooled fluid (viii) a cryogenic fluid, (ix) a resistive heating source coupled to a conductive wire, (x) an ultrasound power source coupled to an ultrasound emitter, wherein the ultrasound power source produces ultrasound energy in the range of about 300 KHZ to about 3 GHz, (xi) and combinations thereof. For ease of discussion for the remainder of this application, the energy delivery device 18 is one or more RF electrodes 18 and the power source utilized is an RF power supply. For these and related embodiments RF power supply delivers 5 to 200 watts, preferably 5 to 100, and still more preferably 5 to 50 watts of electromagnetic energy is to the electrodes of energy delivery device 18 without impeding out. The electrodes 18 are electromagnetically coupled to energy source 20. The coupling can be direct from energy source 20 to each electrode 18 respectively, or indirect by using a collet, sleeve and the like which couples one or more electrodes to energy source 20.

Figure 10:
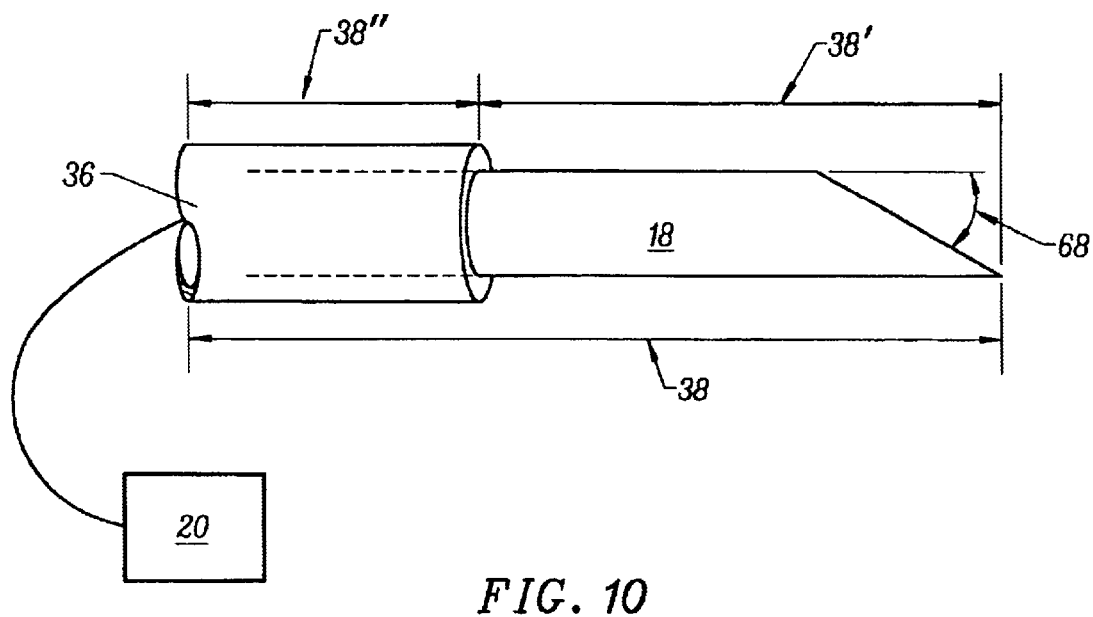
FIG. 10 is a lateral view illustrating the cut angle of the electrode tip.
Figure 11:
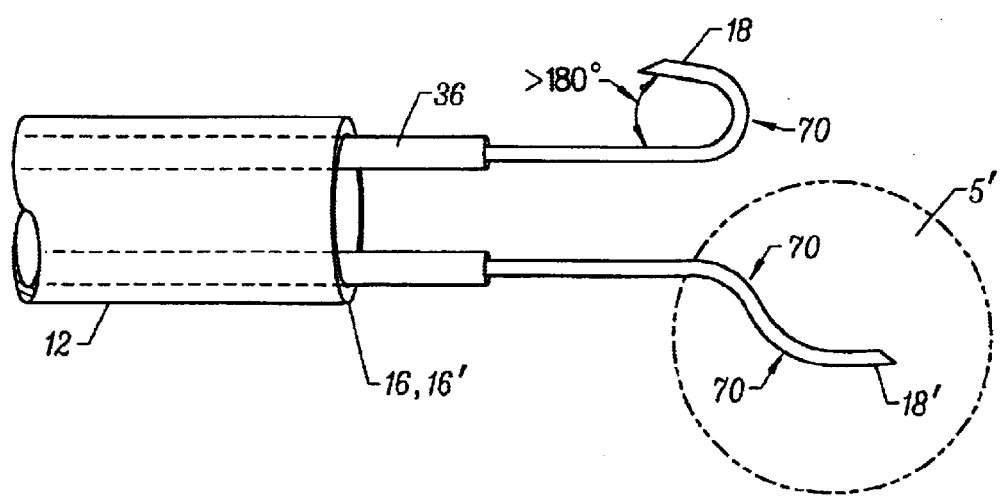
FIG. 11 is a lateral view illustrating an electrode having a radius of curvature.

Referring now to FIGS. 9a–11 for a discussion of the electrode, in various embodiments electrode 18 can have variety of shapes and geometries including but not limited to ring-like, ball, hemispherical, cylindrical, conical or needle-like. In an embodiment electrode 18 can be a needle with sufficient sharpness to penetrate tissue and can comprise all or a portion of needle 16 or needle 17. As shown in FIG. 10, the distal end of electrode 18 can have a cut angle 68 which ranges from 1 to 60°, with preferred ranges of at least 25° or, at least 30° and specific embodiment of 25° and 30°. The surface electrode 18 can be smooth or textured and concave or convex. The conductive surface area 38' of electrode 18 can range from 0.05 mm² to 100 cm². Referring to FIG. 11, electrode 18 can also be configured to be flexible and or deflectable having one more radii of curvature 70 which can exceed 180° of curvature. In use electrode 18 can be configured and positioned to seal and/or treat (via ablative hyperthermia and/or ohmic heating) any selected target tissue volume 5'.

Electrode 18 can have different lengths 38 that are advanced from distal end 16' of introducer 12. The lengths can be determined by the actual physical length of electrode(s) 18, the length of an energy delivery surface 38' of electrode 18 and the length, 38" of electrode 18 that is covered by an insulator. Suitable lengths 38 include but are not limited to a range from 1–30 cms with specific embodiments of 0.5, 1, 3, 5, 10, 15 and 25.0 cm. The actual lengths of electrode 18 depends on the location of tissue site 5' to be ablated, its distance from the site, its accessibility as well as whether or not the physician chooses a bronchioscopic, percutaneous or other procedure.

Figure 12:
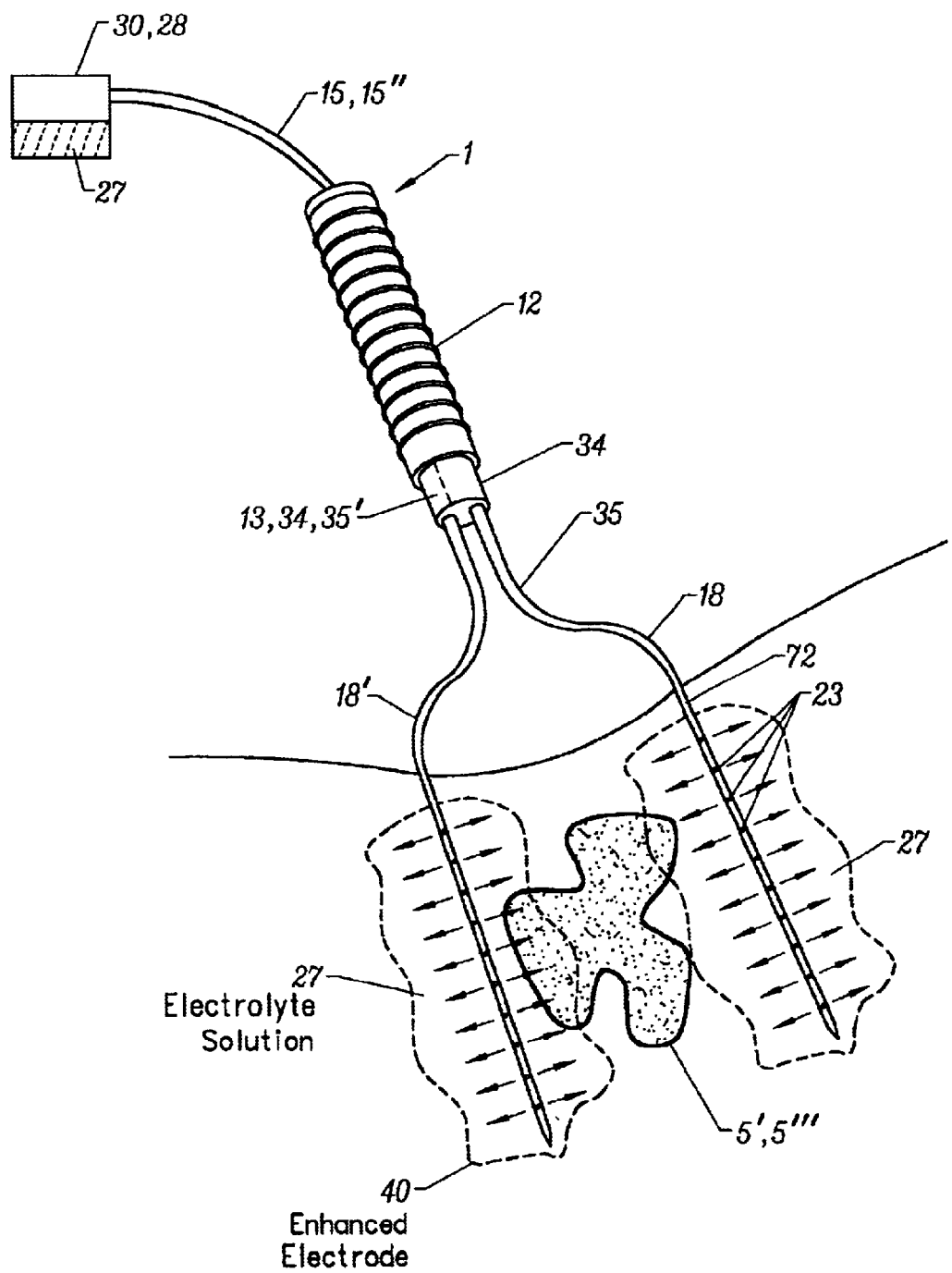
FIG. 12 is a lateral view illustrating an embodiment of an electrode having a lumen and apertures for the delivery of fluid and the use of infused electrolytic fluid to create an enhanced electrode.

Referring now to FIG. 12, electrode 18 can include one or more lumens 72 (which can be contiguous or the same as lumen 13) coupled to a plurality of fluid distribution ports 23 (which can be apertures 23) from which a variety of fluids 27 can be introduced, including electrolytic solutions, cooling fluids, cryogenic fluids chemotherapeutic agents, medicaments, gene therapy agents, contrast agents, infusion media and the like. This is accomplished by having ports or apertures 23 fluidically coupled to one or more lumens 13 which in turn can be coupled to fluid reservoir 30 and fluid delivery device 28. In specific embodiments, ports 23 can be configured to provide cooling of one or both of electrodes 18, 18' and surrounding tissue to prevent tissue from the development of excessive impedance at electrode 18 from the deposition of charred tissue on the surface of electrode 18. Also, the use of infused electrolytic solution 27 allows for the development of an enhanced electrode 40 allowing the treatment of a larger volume of target tissue without impedance-related shut downs.

Figure 13:
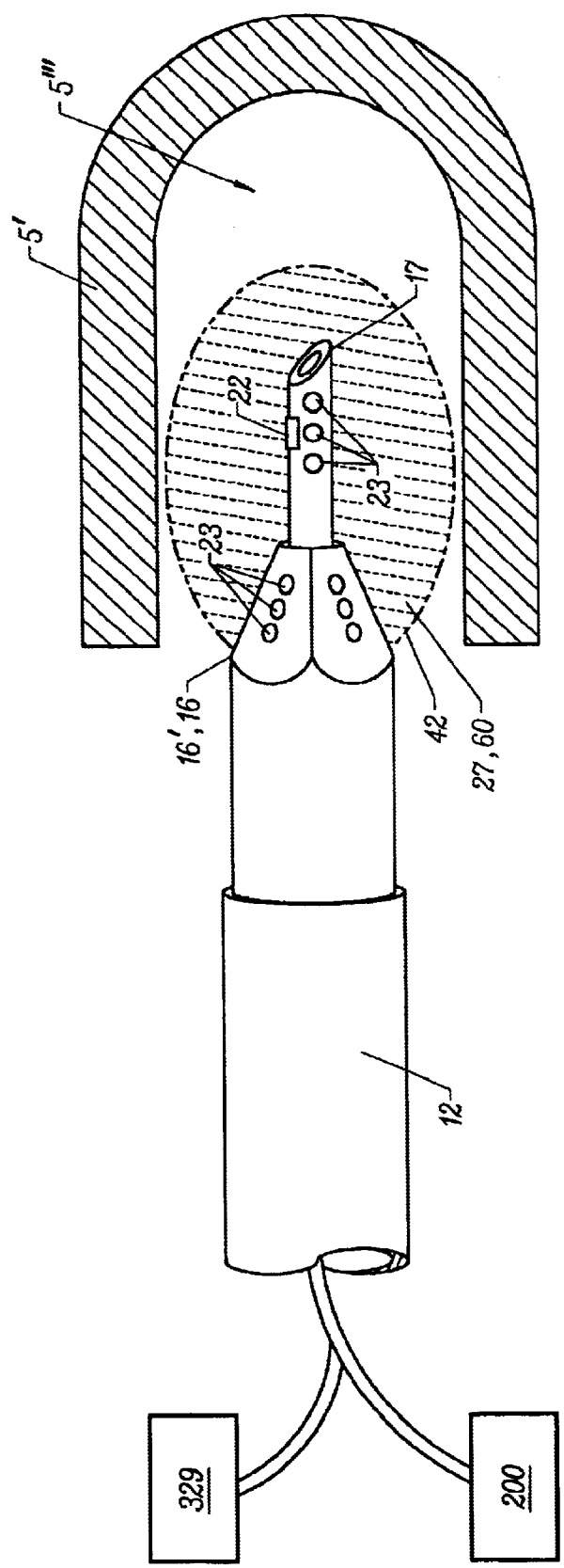
FIG. 13 is a lateral view illustrating an embodiment of the first and second needles configured to infuse a fluid.

Referring now to FIG. 13, in various embodiments, both needle 16 and needle 17 can be configured to infuse a fluid 27 into target tissue site 5' including void space 5'". This can be accomplished through the use of fluid ports or apertures 23. In a specific embodiment, needle 16 can be configured to infuse a fluid into the target tissue site 5' before, during or after the collection of a tissue sample 5" by needle/device 17. In use such infusion permits fluid to quickly fill the void space 5'" and seal the void space 5'". This can be accomplished through use of a curable polymer fluid/sealing agent 60 (described herein) or the use of an electrolytic solution to conduct the delivery of electromagnetic energy (e.g. RF or microwave) to the void space to shrink and/or coagulate surrounding tissue and/or blood so as to form a seal 64 within and/or around the void space 5'". Also as described above, preinfusing electrolytic agent into the treatment site allows the creation of enhanced electrode 40 within the treatment site 5' to rapidly deliver energy to a selectable volume of tissue 42 including void space 5'"so as to seal void space 5'". Tissue volume 42, also called infused volume 42, can be made visually observable/imagable through the use of contrast solutions/agents in electrolytic fluid 27 and imaging system 200 described herein.

Electrode 18 can be made of a variety of conductive materials, both metallic and non-metallic. Suitable materials for electrode 18 include, steel such as 304 stainless steel of hypodermic quality, platinum, gold, silver and alloys and combinations thereof. Also, electrode 18 can be made of conductive solid or hollow straight wires of various shapes such as round, flat, triangular, rectangular, hexagonal, elliptical and the like. In a specific embodiment all or portions of electrodes 18 and 18' can be made of a shaped memory metal, such as NiTi, commercially available from Raychem Corporation, Menlo Park, Calif. A radiopaque marker 11 can be coated on electrodes 18 for visualization purposes.

Electrode 18 can be coupled to any portion of needle 16 using soldering, brazing, welding, crimping, adhesive bonding and other joining methods known in the medical device arts. Also, electrode 18 can include one or more coupled sensors 22 to measure temperature and impedance (both of the electrode and surrounding tissue), voltage and current other physical properties of the electrode and adjacent tissue. Sensors 22 can be at exterior surfaces of electrodes 18 at their distal ends or intermediate sections.

Figure 14A:
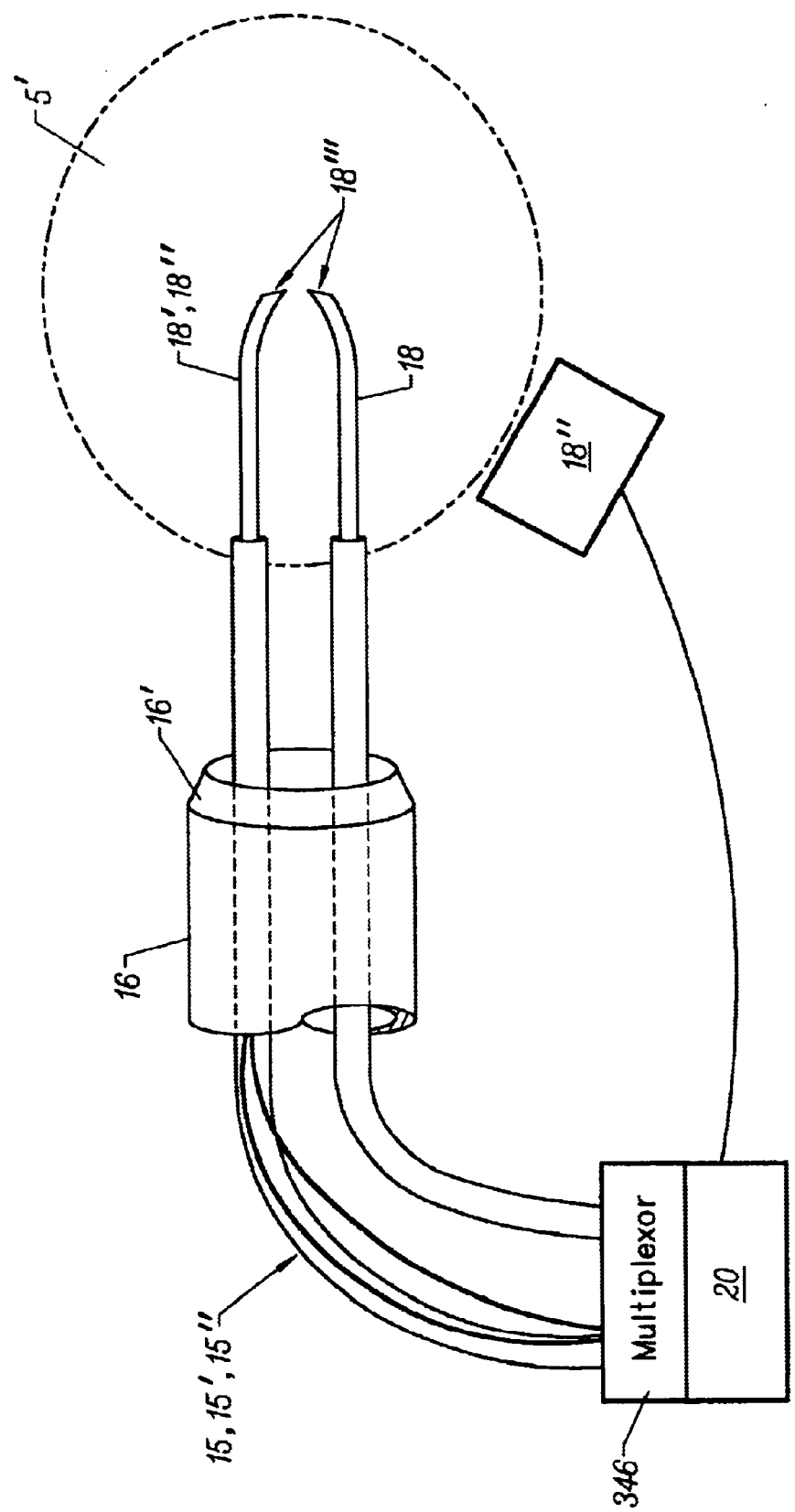
FIG. 14a is a lateral view illustrating an embodiment having multiple electrodes coupled to the first needle.
Figure 14B:
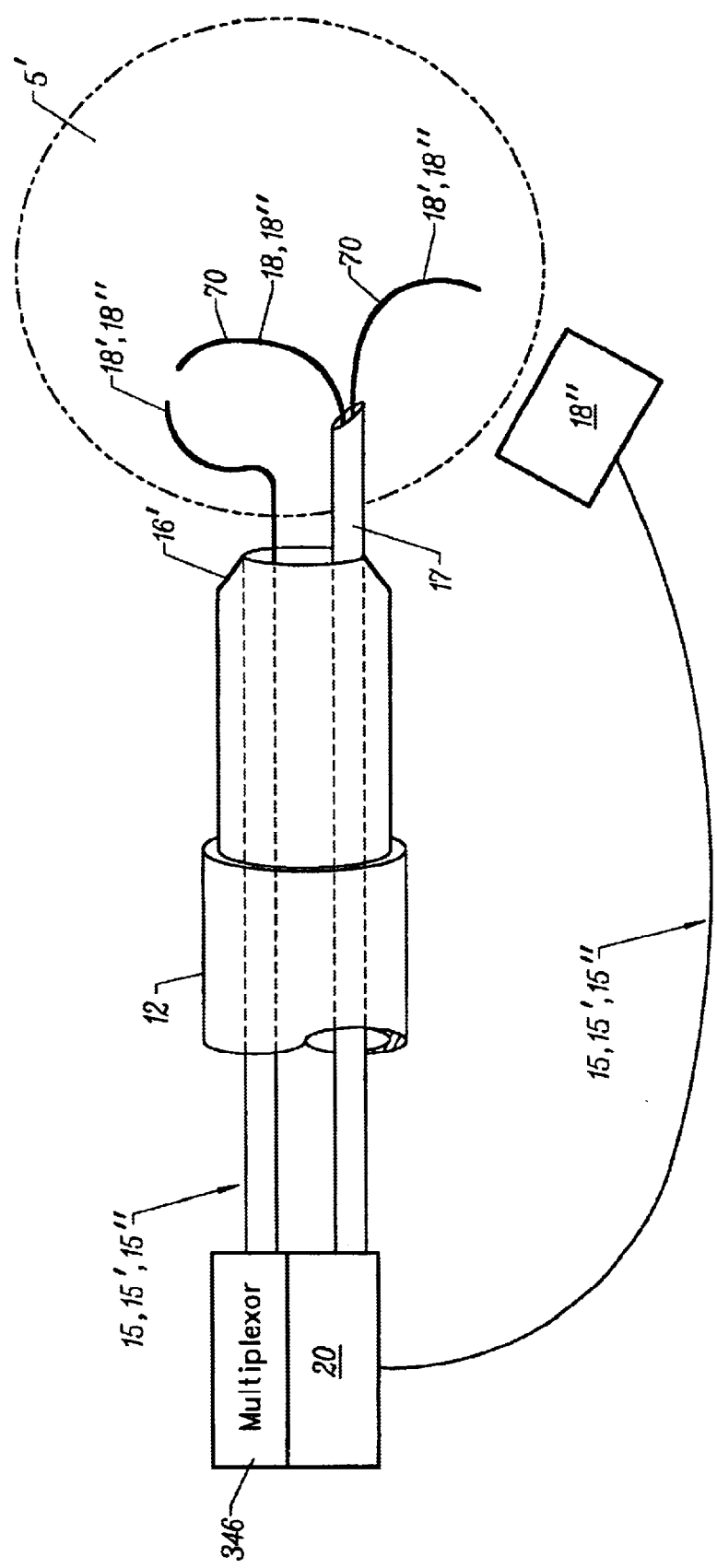
FIG. 14b is a lateral view illustrating an embodiment having electrodes coupled to the first needle and second needles as well as a power supply and ground electrode.

Referring to FIGS. 14a–14b, in various embodiments electrode 18 can comprise two or more electrodes 18 attached to needle 16 to allow for bipolar electrode configurations and/or an array of electrodes 18'" (either bipolar or monopolar). In a related embodiment shown in FIG. 14b, at least one electrode 18 can be coupled to needle 16 and second electrode 18' can be coupled to needle 17 to allow for bipolar energy RF energy delivery to a selectable target tissue volume 5' lying between needles 16 and 17. Electrodes 18 and 18' can be coupled to power supply 20 and/or ground pad electrode 18" via an insulate wire 15' which can be guidewire 15 which can in a specific embodiments be a coaxial cable 15" allowing for coupling of one or both electrodes 18 and 18' to power supply 20 as a ground pad electrode 18". Wires 15' and 15" can also be coupled to a multiplexing device described herein. In use, electrodes 18 and 18' can configured and deployed to seal and/or treat (via ablative hyperthermia and/or ohmic heating) a selectable target tissue volume 5'.

The selectable deployment of electrode 18 can be achieved through one or more of the following approaches (i) the amount of advancement of electrode 18 from introducer 12; (ii) independent advancement of electrode 18 from introducer 12; (iii) the lengths and/or sizes of energy delivery surfaces of electrodes 18 and 18'; (iv) variation in materials used for electrode 18; and (v) variation of the geometric configuration of electrode 18 in their deployed states.

Figure 15A:
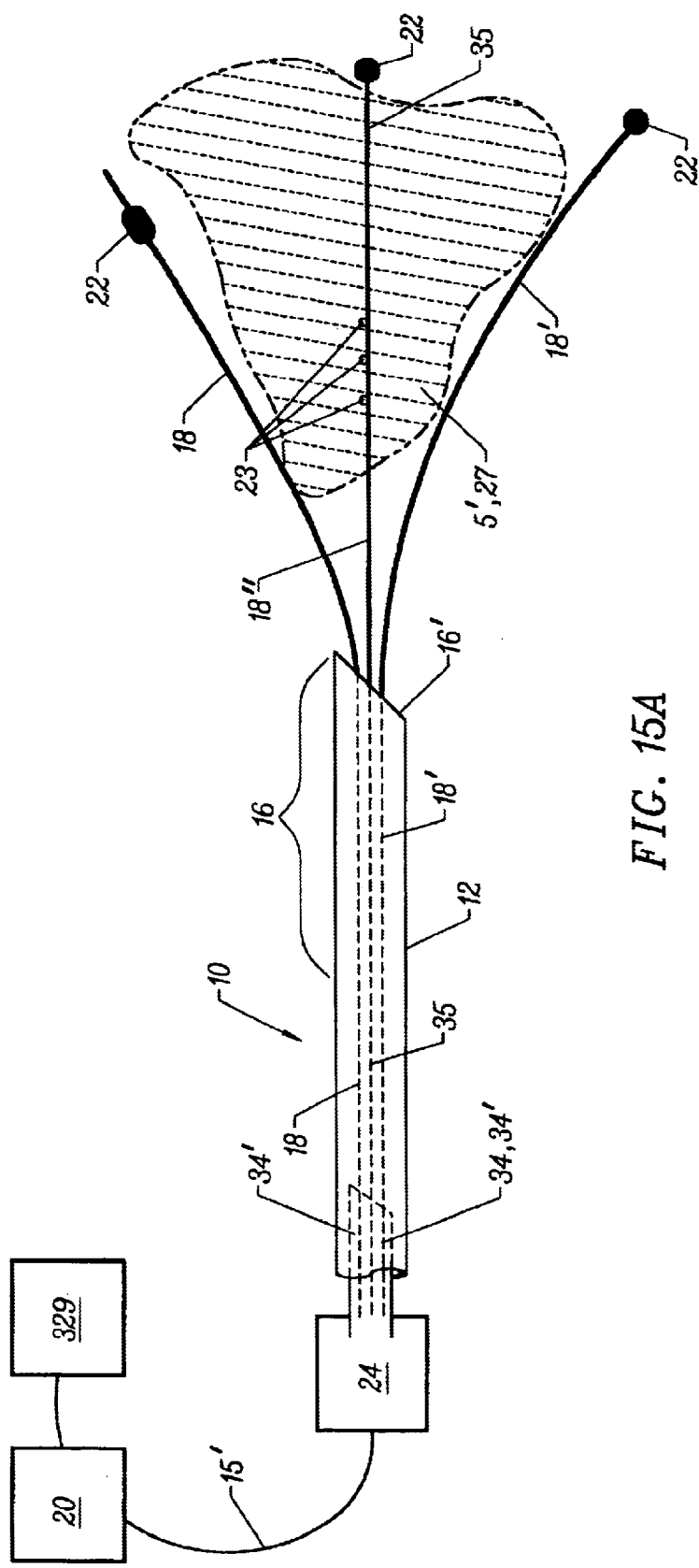
FIG. 15a is cross-sectional view of a lung treatment apparatus of the present invention with two deployable electrodes and a deployable member at a selected cell necrosis tissue site.
Figure 15B:
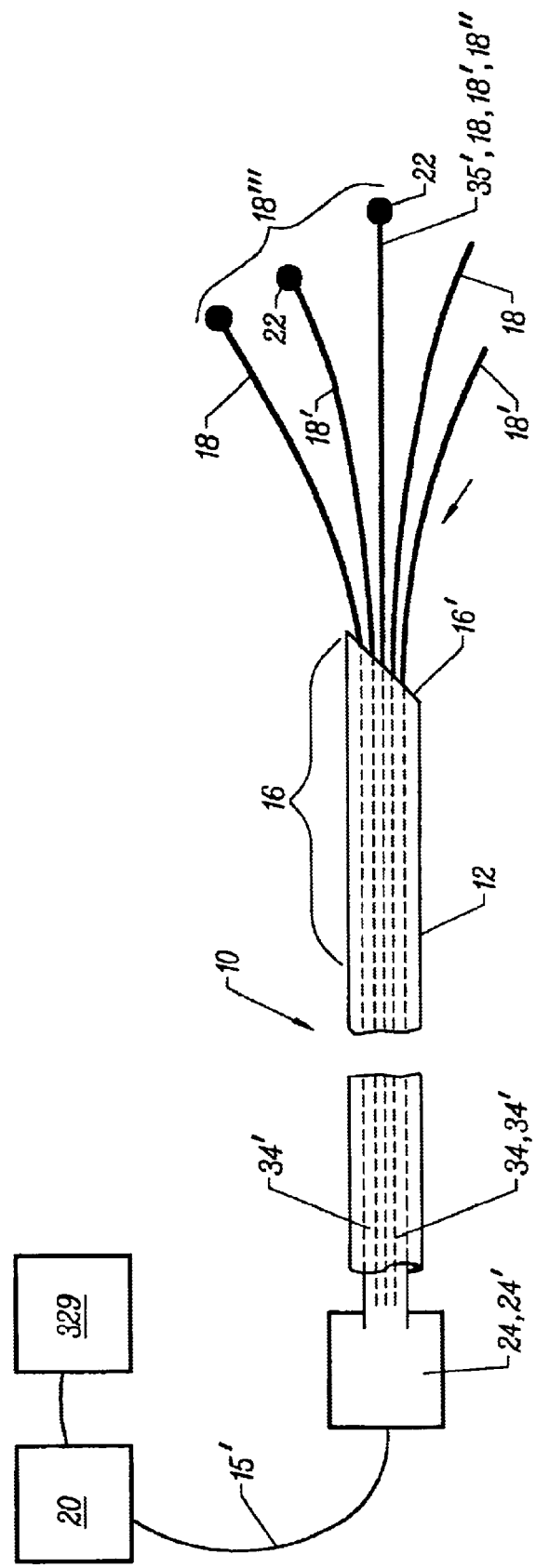
FIG. 15b illustrates a cross-sectional view of an embodiment of a cell necrosis apparatus of the present invention with a first and a second set of deployable electrodes.
Figure 16:
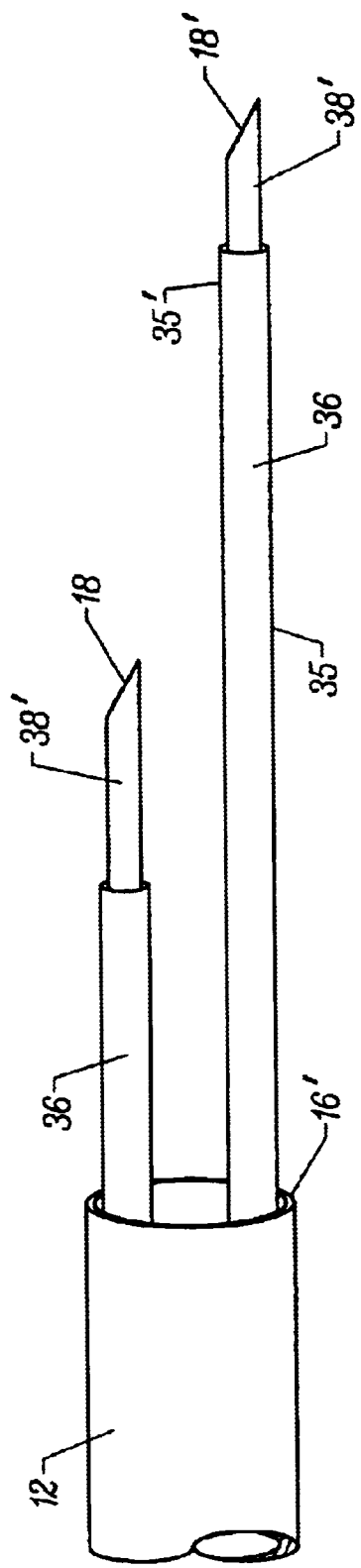
FIG. 16 is a perspective view of a lung treatment apparatus of the present invention that includes insulation sleeves positioned at exterior surfaces of the electrodes.

Referring now to FIGS. 15a–15b, electrodes 18 and 18' can be configured to have a compacted positions while they are positioned in introducer 12. As electrodes 18 and 18' are advanced from introducer 12 they move to a deployed state from their compacted configurations. Any number of electrodes can be included in energy delivery device 18. The electrodes of energy delivery device 18 can be deployed simultaneously, in pairs, in sets and one at a time. The deployable electrodes 18 are configurable to allow volumetric cell necrosis to proceed from the interior, exterior of tissue site 5' as well as various combinations thereof in order to create a selectable and predictable cell necrosis.

In other embodiments electrodes 18 and 18' can be advanced via means of a separate advancement member 34 positionable in introducer 12 (e.g. via lumens 13) and may be coupled to an actuator 24" to allow for selectable and controlled advancement of electrode 18 out of introducer 12 and into a selected depth in target tissue site 5'. In an embodiment, advancement member 34 can be a catheter 34 having one or more lumens 34' for advancement of wires 15, 15' and 15" and electrodes 18 as well as for the introduction and infusion of fluids 27 including electrolytic solutions, chemotherapeutic agents, drugs, medicaments, gene therapy agents, contrast agents and the like.

A deployable member 35 can be coupled to electrode advancement member 34. Deployable member 35 can be configured to provide a variety of different functions including but not limited to the placement of a sensor at a selected tissue site to measure/monitor temperature and/or impedance. Additionally, all or a portion, of deployable member 35 can be an RF electrode operable in either bi-polar or mono-polar modes. Deployable member 35 can also be a groundpad electrode. A sensor 22 can be coupled to deployable member 35 at a distal end 35', or at any physical location of deployable member 35. In this manner, temperature and/or impedance is measured or monitored at a distal portion of tissue site 5' or at any position in or external to tissue site 5'.

Electrodes 18 and 18' can be selectably deployable from introducer 12 or deployable member 35 with curvature to create any desired geometric area of cell necrosis. The selectable deployment is achieved by having electrodes 18 with, (i) different advancement lengths from introducer 12, (ii) different deployed geometric configurations, (iii) variations in cross-sectional geometries, (iv) selectable insulation provided at each and/or all of the deployed electrodes 18, or (v) the use of adjustable insulation. Deployed electrodes 18 and/or 18' can create a variety of different geometric cell necrosis zones including but not limited to spherical, semi-spherical, spheroid, triangular, semi-triangular, square, semi-square, rectangular, semi-rectangular, conical, semi-conical, quadrilateral, semi-quadrilateral, rhomboidal, semi-rhomboidal, trapezoidal, semi-trapezoidal, combinations of the preceding, geometries with non-planar sections or sides, free-form and the like.

Referring now to FIGS. 16–19, in various embodiments, one or more electrodes 18, as well as deployable member 35, can have an exterior surface that is wholly or partially insulated and provide a non-insulated area which is an energy delivery surface. In the embodiment shown in FIG. 16, electrodes 18 can include insulation 36. In the embodiment of FIG. 8, insulation 36 is an insulation sleeve 36 that can be fixed or adjustable. The active area of electrodes 18 is non-insulated and provides an energy delivery surface 38'.

Figure 17:
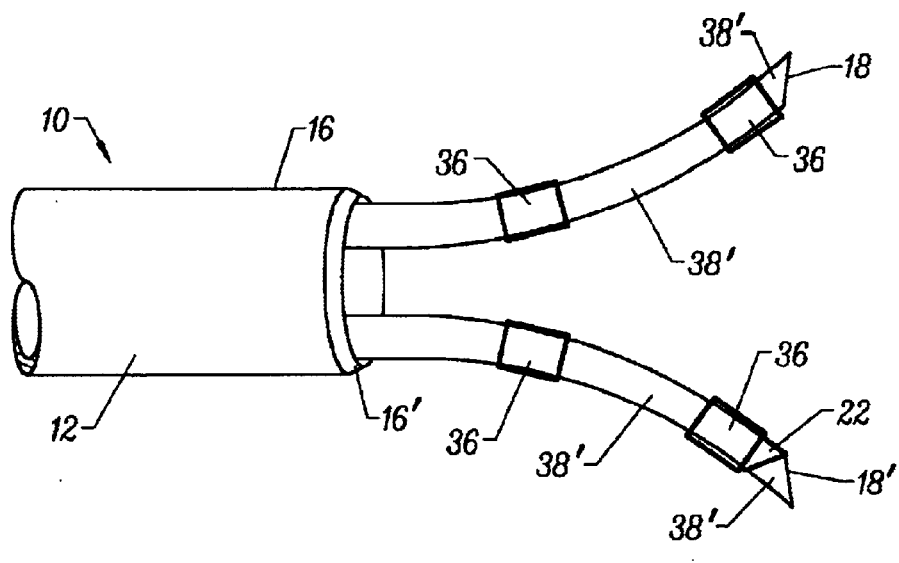
FIG. 17 is a perspective view of a lung treatment apparatus of the present invention that includes multiple insulation sleeves that circumferentially insulate selected sections of the electrodes.

In the embodiment illustrated in FIG. 17, insulation 36 is formed at the exterior of electrodes 18 in circumferential patterns, leaving a plurality of energy delivery surfaces 38' which can be ring shaped distributed over the length of electrode 18.

Figure 18:
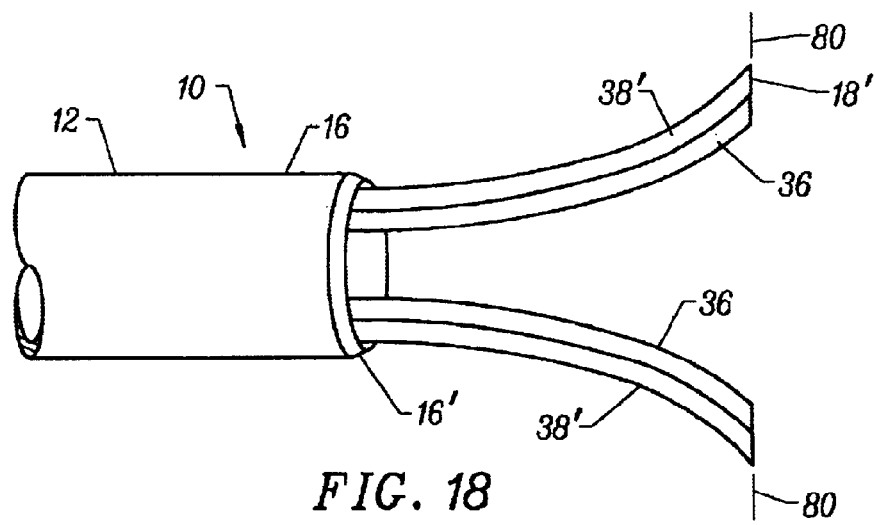
FIG. 18 is a perspective view of a lung treatment apparatus of the present invention with insulation that extends along longitudinal sections of the electrodes to define adjacent longitudinal energy delivery surfaces.
Figure 19:
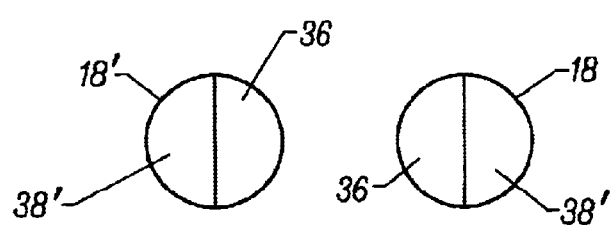
FIG. 19 is a cross-sectional view of the cell necrosis apparatus of FIG. 18 taken along the lines 18—18.

Referring now to the embodiment of FIGS. 18 and 19, insulation 36 extends along a longitudinal exterior surface of electrodes 18. Insulation 36 can extend along a selected distance along a longitudinal length of electrodes 18 and around a selectable portion of a circumference of electrodes 18. In various embodiments, sections of electrodes 18 can have insulation 36 along selected longitudinal lengths of electrodes 18 as well as completely surround one or more circumferential sections of electrodes 18. Insulation 36 positioned at the exterior of electrodes 18 can be varied to define any desired shape, size and geometric energy delivery surface 38'.

Figure 20:
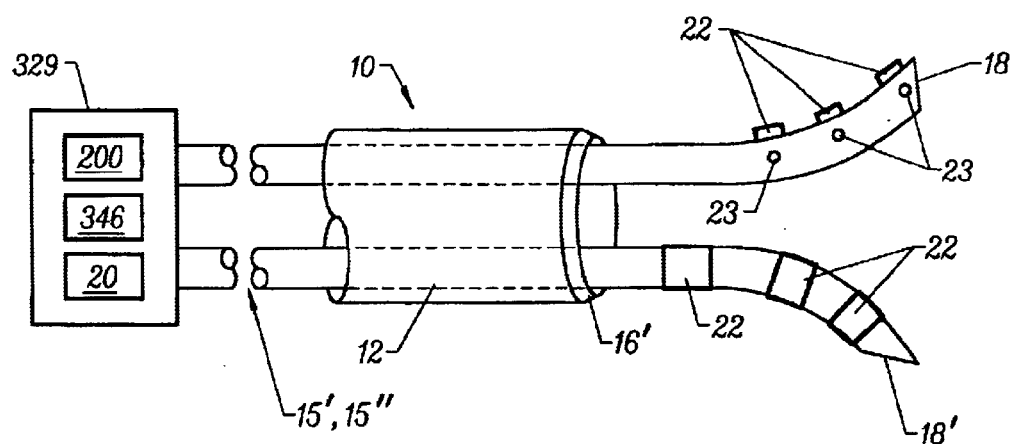
FIG. 20 illustrates an embodiment of a lung treatment apparatus with multiple sensors coupled to electrodes.

Turning to a discussion of sensors, the use of one or more sensors 22 coupled to the introducer, energy delivery devices, deployable member and biopsy needles and permits accurate measurement of temperature at tissue site 5' in order to determine, (i) the extent of cell necrosis, (ii) the amount of cell necrosis, (iii) whether or not further cell necrosis is needed and (iv) the boundary or periphery of the ablated tissue mass. Further, sensor 22 reduces non-targeted tissue from being injured, destroyed or ablated. Referring to FIG. 20, multiple sensors can be coupled to electrodes 18.

Sensor 22 can be selected to measure temperature, tissue impedance or other tissue property described herein to permit real time monitoring of energy delivery. This reduces damage to tissue surrounding the targeted mass to be ablated. By monitoring the temperature at various points within and outside of the interior of tissue site 5', a determination of the selected tissue mass periphery can be made, as well as a determination of when cell necrosis is complete. If at any time sensor 22 determines that a desired cell necrosis temperature is exceeded, then an appropriate feedback signal is received at an energy source 20 coupled to energy delivery device 18 which then regulates the amount of electromagnetic energy delivered to electrodes 18 and 18'.

Sensor 22 can be of conventional design, including but not limited to thermal sensors, acoutiscal sensors, optical sensors, pH sensors, gas sensors, flow sensors positional sensors and pressure/force sensors. Thermal sensors can include thermistors, thermocouples, resistive wires, optical sensors and the like. A suitable thermal sensor 22 includes a T type thermocouple with copper constantene, J type, E type, K type, fiber optics, resistive wires, thermocouple IR detectors, and the like. Acoustical sensors can include ultrasound sensors including piezoelectric sensors which can be configured in an array. Pressure and force sensors can include strain gauge sensors including silicon-based strain gauges. Optical sensors can include photomultipliers and micro-machined optical fibers. Gas sensors can include O2 sensors such as Clark electrodes, CO2 sensors and other electrochemical based sensors known in the art. Flow/velocity sensors can include ultrasound sensors, electromagnetic sensors and aneometric sensors which can be configured to detect both liquid and gaseous flows. Positional sensors can include LVDT's, and Hall effect sensors. Other sensors which can be employed impedance sensors, antibody-based sensors, biosensors (e.g. glucose) and chemical sensors. In various embodiments one sensor can be configured to detect multiple parameters or one or more sensors can be coupled together. Pressure sensors can be selected and/or configured to detect pressure differentials less than 1 mmHg and even less than 0.1 mmHg. In specific embodiments, pressure sensor 22 can be a micro-machined fiber optic sensor, a PSP-1 pressure sensors made Gaymar Industries Inc., (Orchard Park, N.Y.) or a Monolithic Integrated Pressure sensor made by the Fraunhofer-Institut (Duisburg, Germany). Also, ultrasound sensor or transducers can be a Model 21362 imaging probe by the Hewlett Packard Company, Palo Alto, Calif.

Figure 21:
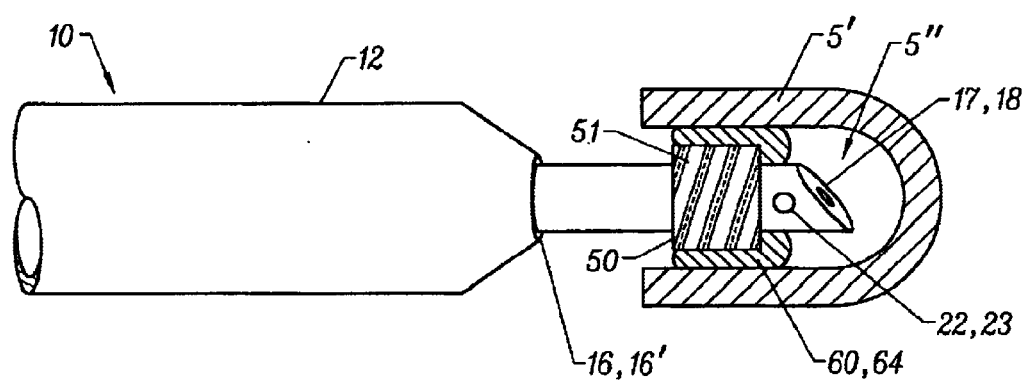
FIG. 21 is a lateral view illustrating an embodiment of the lung treatment apparatus having a closure device.

Referring now to FIG. 21, in various embodiments apparatus 10 can be configured for the delivery of one or more closure devices 50 at or adjacent the selected tissue site 5' including void space 5''', tissue interface. The closure device 50 can serve to hold and/or clamp the edges of tissue void together to produce an immediate tight seal, including an air tight seal, promote healing at the tissue interface, ensure long term reliability of the seal and healed interface. In various embodiments closure device 50 can be a suture, a butterfly suture, a surgical mesh or membrane, a wire mesh, a surgical staple, a coiled spring, a leaf spring, a shaped spring, a miniature surgical clamp or clip, a miniature hemostat, an inflatable balloon, a shaped inflatable balloon or a wedge or plug of resilient material.

Closure device 50 can be configured to be left in permanently, removed during the procedure or removed at a later time. All or portions of closure device 50 can be electrically or thermally conductive to facilitate delivery of RF and or thermal energy to the tissue interface and/or surrounding tissue to facilitate sealing via tissue coagulation and collagen shrinkage. Also all or a portion of closure device 50 can be constructed of radio-opaque or echogenic to facilitate identification of device 50 using imaging system 200 described herein. These materials can include radio-opaque/echogenic markers 51 positioned at selectable locations on device 50. In various embodiments all or a portion of closure device 50 can be constructed of bioabsorbable material which are absorbed and/or ingrown by tissue over period of days or months.

In use, closure device 50 can be deployed before, during or after the collection of a tissue sample from target tissue site 5'. In preferred embodiments, closure device 50 is deployed simultaneously or immediately after the collection of the tissue sample and may be accompanied by concomitant delivery of a sealing agent 60 and energy to fill and fludically seal any void spaces 5''' in and around closure device 50 and the tissue collection void space or any adjacent tears caused by the biopsy collection process.

Referring now to FIGS. 22a and 22b, in an embodiment closure device 50 is a coiled spring 52 with a selectable pitch 53, inner and outer diameter 54 and 55. Spring 52 can be configured to have sufficient spring force (0.01 to 0.5 lbs) to clamp and/or hold sections of blood vessels 9 and adjacent lung tissue layers together including coagulation and/or healing occurs and if necessary with sufficient force to maintain an air-tight, liquid-tight seal. Spring 52 can be prewound to a smaller diameter before being disposed on introducer 12 in a delivery configuration with a larger diameter and have sufficient spring force/and or shape memory to reassume its smaller diameter upon deployment. Similarly, spring 52 can be prewound to a larger diameter and put in a delivery configuration in a smaller diameter and reassume its original diameter upon deployment and imparted and positioned over distal portion of introducer 12.

In an embodiment shown in FIG. 22b, closure device 50 is a tapered coiled spring with a tapered end 56 (which can be marked with a radio-opaque marker 51) and taper or contour 57. Tapered spring can be positioned on introducer 12 with tapered end 56 oriented either towards introducer distal end 16' or proximal end 14. In one embodiment spring 52 is threaded onto the distal end of introducer 12 with the tapered end 56 oriented distally and deployed by turning and or twisting introducer 12 to wind off the spring in a distal direction at the selected tissue site. In these and related embodiments the tapered spring end 56 can have sufficient sharpness and pitch to penetrate tissue and/or act like a cork screw. In another embodiment spring 52 can be deployed by being advanced off introducer 12 using another introducing member, an inflatable balloon or other deployment mechanism/device known in the art of stent technology.

Figure 23A:
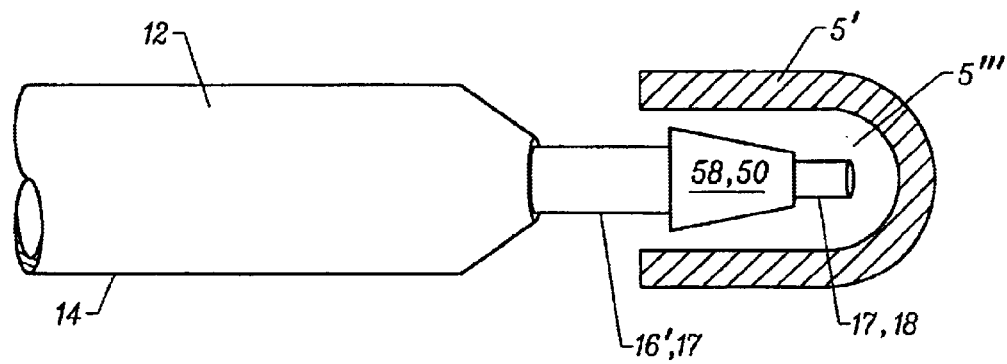
FIGS. 23a, 23b and 23c are lateral views illustrating an embodiment of a tissue plug closure device and its deployment.
Figure 23B:
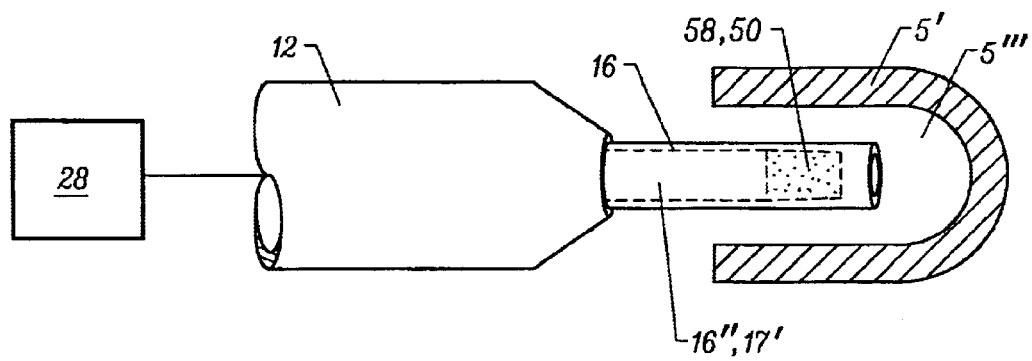
Figure 23C:
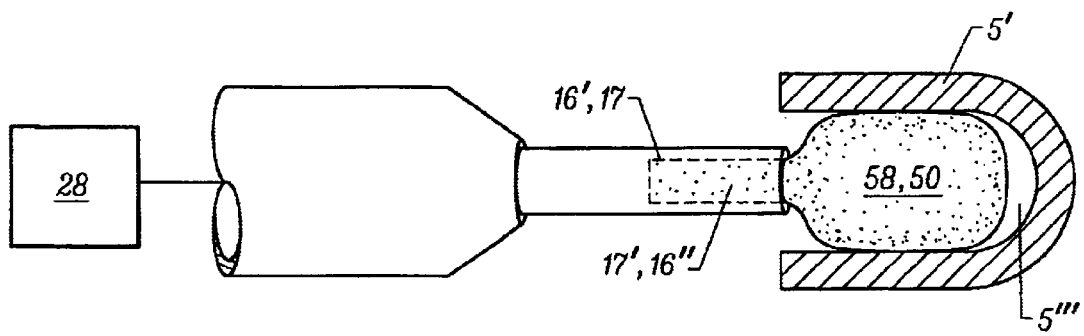

Referring now to FIGS. 23a–23c, in other embodiments closure device 50 can be a plug 58 or tissue plug 58. Plug 58 can have a selectable shape including, but not limited to, rectangular, cylindrical, pyramidal wedge shaped and combinations thereof. Plug 58 can made of a resilient biocompatible material such as an elastomer (e.g. silicone) which is contained within introducer 12 in a compressed or non deployed state and then extruded or ejected out into the selectable tissue site and expand into an expanded or deployed state filing a void space 5'''. As shown in FIGS. 23b–23c, plug 58 can be disposed within a lumen or chamber of introducer 12 (in a contracted or compacted state) and then extruded out via means of a pressure source or pumping device 28 coupled to introducer 12. Plug 58 can be made from a variety of biocompatible polymers described herein including elastomers, silicone, polyurethane, PTFE, hydrogels and bioabsorbable materials.

Figure 24:
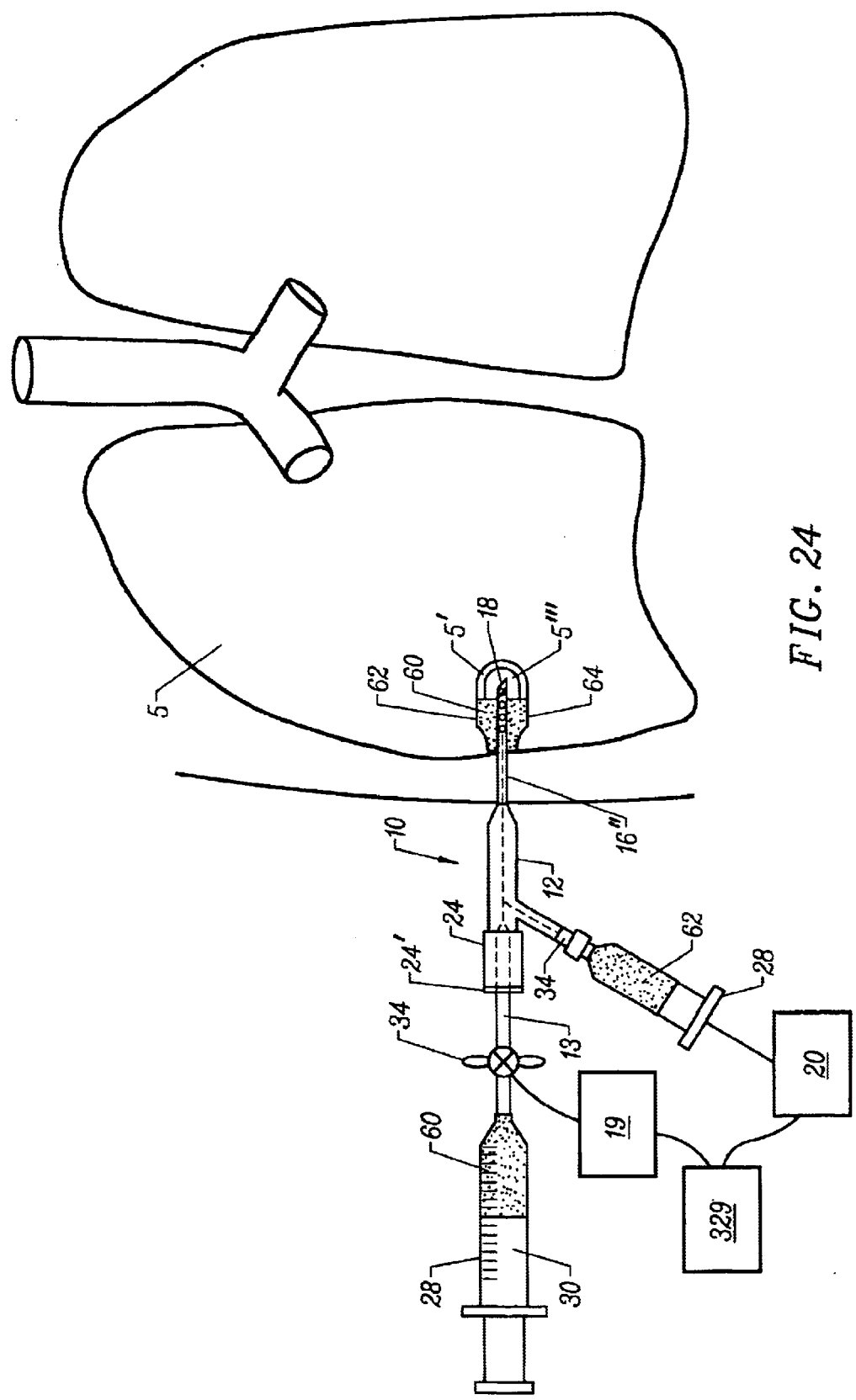
FIG. 24 is a lateral view illustrating embodiments using a sealing agent.

Referring now to FIG. 24, in various embodiments of the invention, a sealing agent 60 can be delivered to the target tissue site before, during or after the delivery of energy or treatment in order to facilitate the forming of a seal 64. Sealing agent 60 can be in liquid, solid or an emulsion form. Sealing agent 60 serves to facilitate the sealing of the tissue site 5' including void 5''' and/or improve the integrity and/or reliability of the seal. Sealing agent 60 can be delivered through a lumen 16" in needle 16 fluidically coupled to an infusion pump, syringe or other fluid delivery device 28 or pressure source. Sealing agent 60 can also be contained in a reservoir 30 or chamber within or coupled to introducer 12 or handpiece 24. In use apparatus 10 can be configured to deliver sealing agent 60 before, during, or after the collection of the biopsy tissue sample form target tissue site 5'. In a preferred embodiment, apparatus 10 is configured to simultaneously or near simultaneously deliver sealing agent 60 to tissue site 5' as the biopsy sample is being collected so as to rapidly back fill any void space as its being created. This can be accomplished through the use a control system described herein or the use of spring 19 and/or servo mechanism which can be configured to open a valve coupling lumen 13 to pumping device 28 and sealant reservoir 30.

After delivery to the target tissue site 5', sealing agent 60 is configured to set up or cure during which one of the following occurs: undergoes a curing and/or polymerization reaction whereby one or both of the following occurs: crosslinks form between adjacent molecular chains of the sealing agent; and the molecular chains of the sealing agent contract along their longitudinal axis resulting in a shortening or shrinkage of the sealing agent in one or more axes. In various embodiments, sealing agent 60 can be configured to set up or cure on its own through contact (cure on contact) with tissue or can include a separate activating agent or catalyst 62 including chemical catalyst. Activating agent 62 can be delivered concurrently with sealing agent 60 or afterwards. Activating agent 62 can also be in the form of energy such as optical energy, ultrasound energy, thermal energy or RF energy. Once cured, sealing agent 60 forms a coagulum with surrounding tissue 5' which can include pulmonary tissue, native collagen and fibrin so as to form a seal 64.

In specific embodiments, sealing agent 60 can be a UV-cured biomedical adhesive such as Ultra Light Weld 1191-M UV/visible light-curing fluorescing adhesive manufactured by the Dymax Corporation (Torrington, Conn.). In related embodiments ahesive agent 60 can be configured to have different and/or descrete optical, radio-opaque, acoustical, echogenic or electrical properties upon curing. This presents the physician the distinct advantage of allowing the physician to ascertain the completeness of curing of the seal and the size of the seal on real time basis using imaging systems described herein or other imaging means known in the art. It can be accomplished by adding indicator agents to sealing agent 60 that change their optical, acoustical or radiopaque properties upon curing. The indicator agents can also be configured to provide a signal and or faciliate detection using imaging system 200 or other means when the seal has been compromised (fluidically or otherwise). Such indicator agents can include but are not limited to microspheres, liposomes and various polymers and polymer emulsion. In specific embodiments, sealing agent 60 can be a ligth-cured biomedical adhesive such as Ultra Light Weld 1191-M UV/visible light-curing fluorescing adhesive manufactured by the Dymax Corporation (Torrington, Conn.). In these embodiments, the energy source can include an optical source which delivers visible or UV light such as Dymax's MediCure MC4000 UV light-curing system.

In various embodiments, sealing agent 60 can be a biomedical polymer known in the art which cures or cross-links in vivo on contact with tissue or via the delivery of energy or an activating agent 62. Preferred curable biomedical polymers include polysiloxanes (e.g. silicones), polyurethanes, hydrogels, polytetrafluoroethylene and copolymers and mixtures thereof. In related embodiments sealing agent 60 can be configured to integrate with the underlying tissue (e.g. coagulum) and /or biodegrade in time after tissue has ingrown the tissue site /void space. Preferred biodegradable polymer sealing agents 60 can include but are not limited to, collagen, gelatin, elastin, fibrinogen, albumin, hydrogels and composites and add mixtures thereof.

In various embodiments seals formed with sealing agent 60 have one or more of the following properties: (i) have sufficient mechanical strength post-curing to maintain tissue integrity during the healing process proceeds; (ii) durability sufficient to provide medical benefit, e.g. usually 3–5 days, on occasion 60+ days (iii) thermal resistance to withstand heating up to 160–170° F., and even tissue boiling; and (iv) have good electrical conductivity to allow energy (electrical, RF, microwave etc.) to go through the developing seal and/or cured seal to surrounding tissue.

In alternative embodiments, sealing agent 60 can be configured (via manipulation of viscoelastic properties, viscocity composition, delivery method, etc.) to be used in conjunction with a mechanical closure device 50 (such as spring 52 or plug 58) disclosed herein. This configuration provides the benefit of additional seal integrity (e.g fluidic seal integrity), strength, durability, etc. to the tissue interface 66 joined by the closure device. In a specific embodiment, sealing agent 60 can be delivered to surround or fill in spaces between the mechanical closure device. In a related embodiment the mechanical closure device can be configured to act like a clamp or vice to apply pressure to hold the tissue interface 66 in place until the sealing agent 60 sets up and the seal has formed. The closure device can then be left in place or removed.

Figure 25:
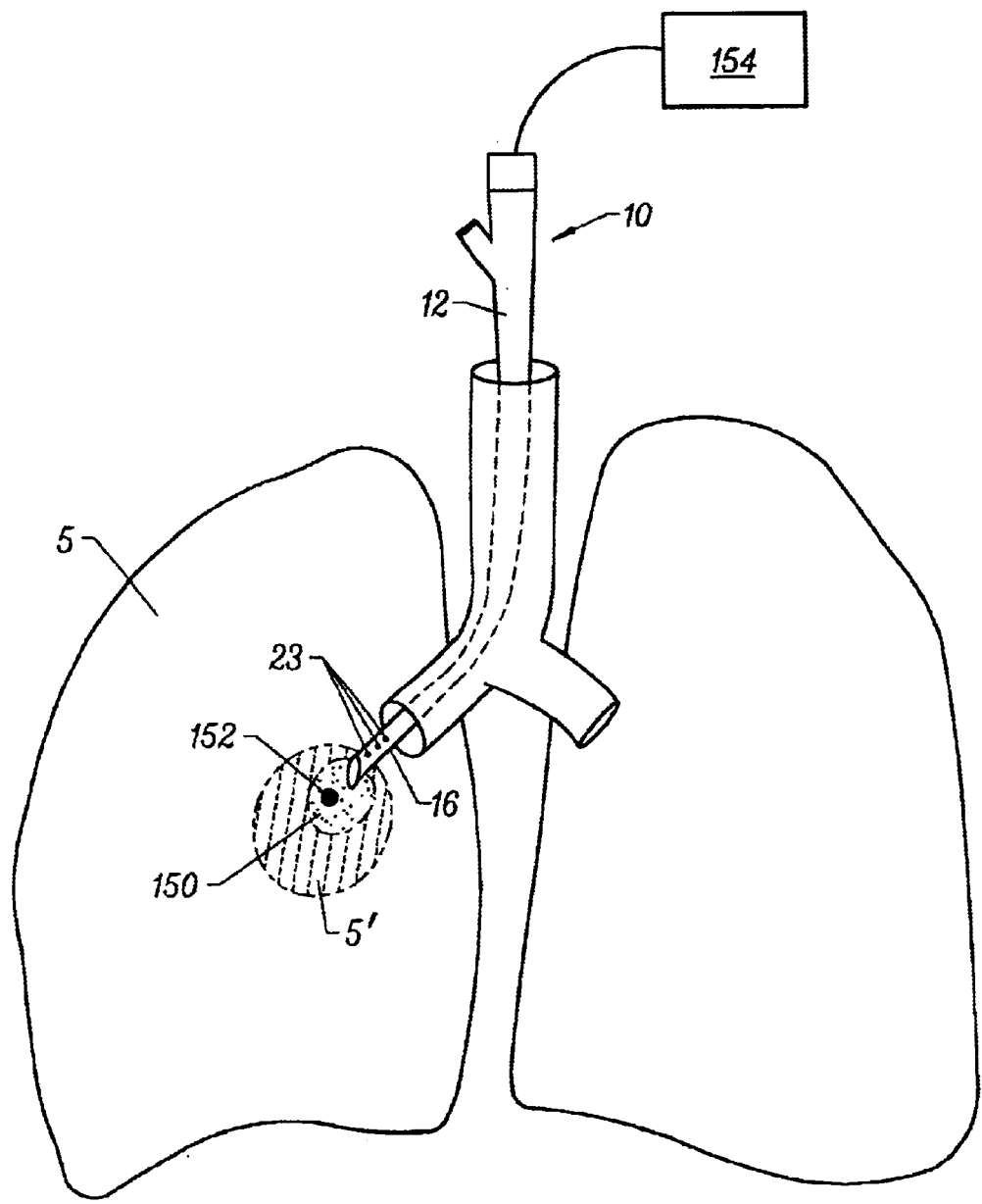
FIG. 25 is a schematic view illustrating the use of gene therapy agents.

Referring now to FIG. 25, in various embodiments, apparatus 10 can be configured for the delivery of gene therapy and gene therapy agents 150 to a selected tissue site 5' in lung 5. Gene therapy agents 150 can include, but are not limited to vectors such as viruses including attenuated versions of the adenovirus, retrovirsues; plasmids, and yeast artificial chromosomes. Plasmids 152 can be delivered in the form of plasma-liposome complexes (a plasmid encapasulated in a liposome ) and the like. A combination of plasmids and viruses or plasmid-virus hybrids can also be employed. The advantages of the adenovirus is its efficiency at gene delivery. Its disadvantage is its toxicity, humoral, cellular, and neurogenic. The advantages to plasmid-liposome complexes are the ease of production and the low toxicity profile. The disadvantage is low efficiency. Accordingly combinations of plasmid and viral vectors can be employed to exploit the advantages and minimize the disadvantages of both systems. In one embodiment a plasmid-virus hybrid can be employed where the virus is delivered in a discrete area by apparatus 10, to minimize toxicity and a liposome-plamid complex is delivered over a larger area using either apparatus 10 or aerosol or inhalation delivery system 154 known in the art. The amounts and/or ratio of adensosine virus (or other virus) to plasmid-lipid complex can be titrated to the specific therapeutic needs of the patient taking into account factors such as the size and type of tumor/lesion, progression of the disease, concurrent medications, patient size and age. Gene therapy agents 150 can be targeted for specific cancer causing genes and related mutations such as mutations on the Rb2/p130 gene and the like. Gene therapy can be delivered using either in vivo or in vitro techniques known in the art.

Figure 26:
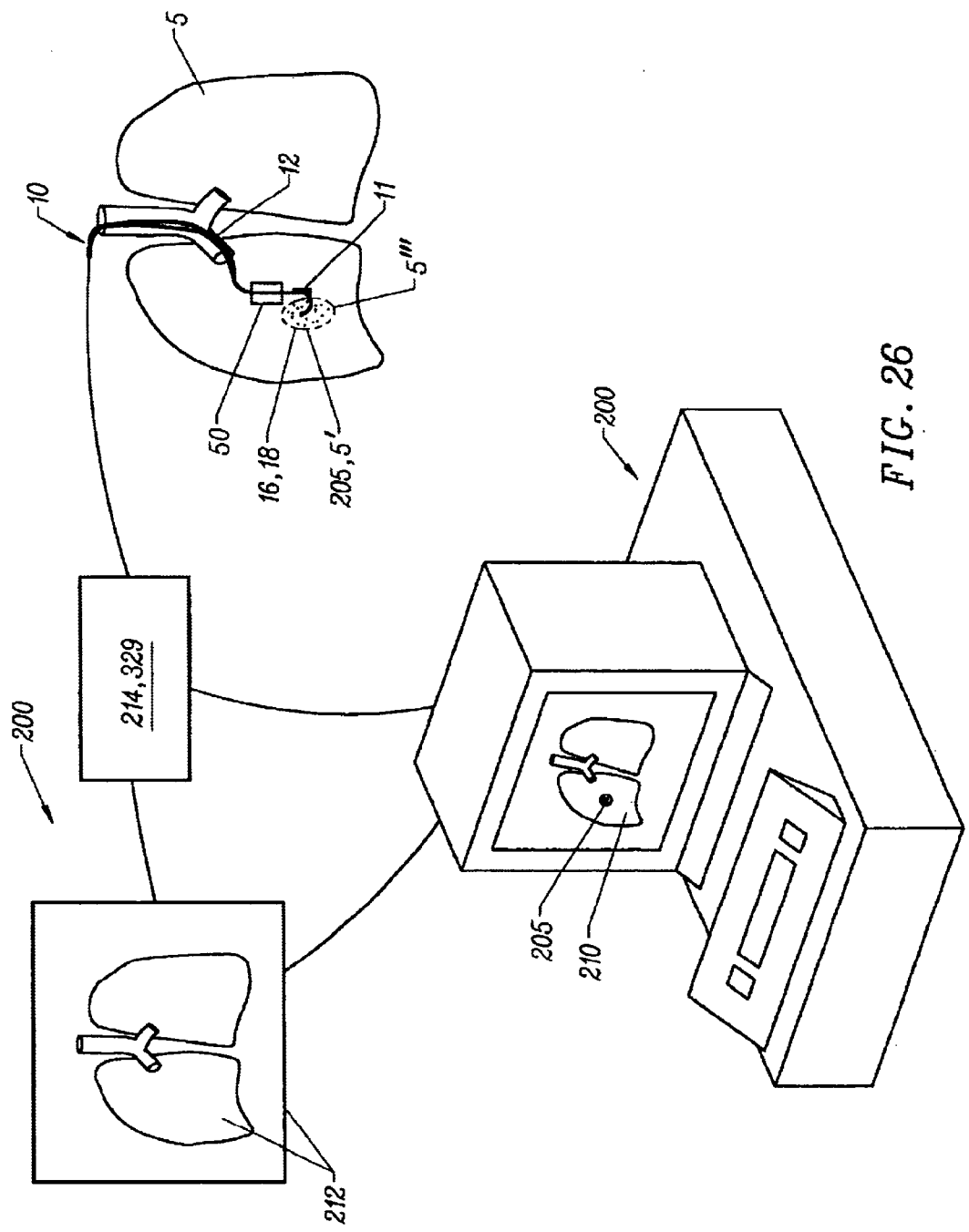
FIG. 26 is a schematic view of an imaging system used with various embodiments of the invention.

Referring now to FIG. 26, in various embodiments, an imaging system 200 can be coupled or otherwise used in conjunction with apparatus 10. Images 210 generated by imaging system 200 can be used to locate and identify the volume of the tumor or target mass of tissue 5' to be treated. Imaging system 200 can also be configured to allow the real time monitoring of the target tissue site 5' before, during, and after the delivery of energy. This allows the volume of a developing lesion 205 (also called ablation volume 205) to be monitored on a real time basis, in turn allowing a more accurate delivery of energy to the target tissue and assuring complete ablation of the disease tissue. Specifically, this provides the advantage of assuring that the entire targeted tumor is treated while reducing the risk of damaging surrounding healthy tissue including the interface/border between healthy and diseased tissue. Also, imaging system 200 can be configured to do one or more of the following: (i) assess/assist the positioning of closure device 50; (ii) assess/assist the delivery of sealing agent and its state of cure; (iii) detect for void spaces 5''', particularly those likely to cause pneumothorax; and (iv) monitor for leaks via the use of doppler ultrasound imaging. Pretreatment images 212 of the target tissue site can be digitally stored within memory resources 214 resident or coupled to imaging system 200 or a computer system described herein and used to accurately assess clinical and subclincial endpoints of treatment.

Suitable imaging systems include but are not limited to, ultrasound, positron emission tomagraphy, CT scanning including fast CT scanning, X-ray film, X-ray fluoroscope, magnetic resonance imaging, electromagnetic imaging and the like. The coupling of imaging system 200 with the use of radiopaque, and/or ecogenic markers 11 on apparatus and closure device 50 can be used to leverage and improve the resolution, procedure time, safety, diagnostic accuracy and therapeutic effect of the selected treatment procedure.

In embodiments using ultrasound imaging, an ultrasound transducer transmits ultrasound energy into a region of interest in a patient's body. The ultrasound energy is reflected by different organs and different tissue types. Reflected energy is sensed by the transducer, and the resulting electrical signal is processed to provide an image of the region of interest. In this way, the volume to be ablated is ascertained.

Figure 27:
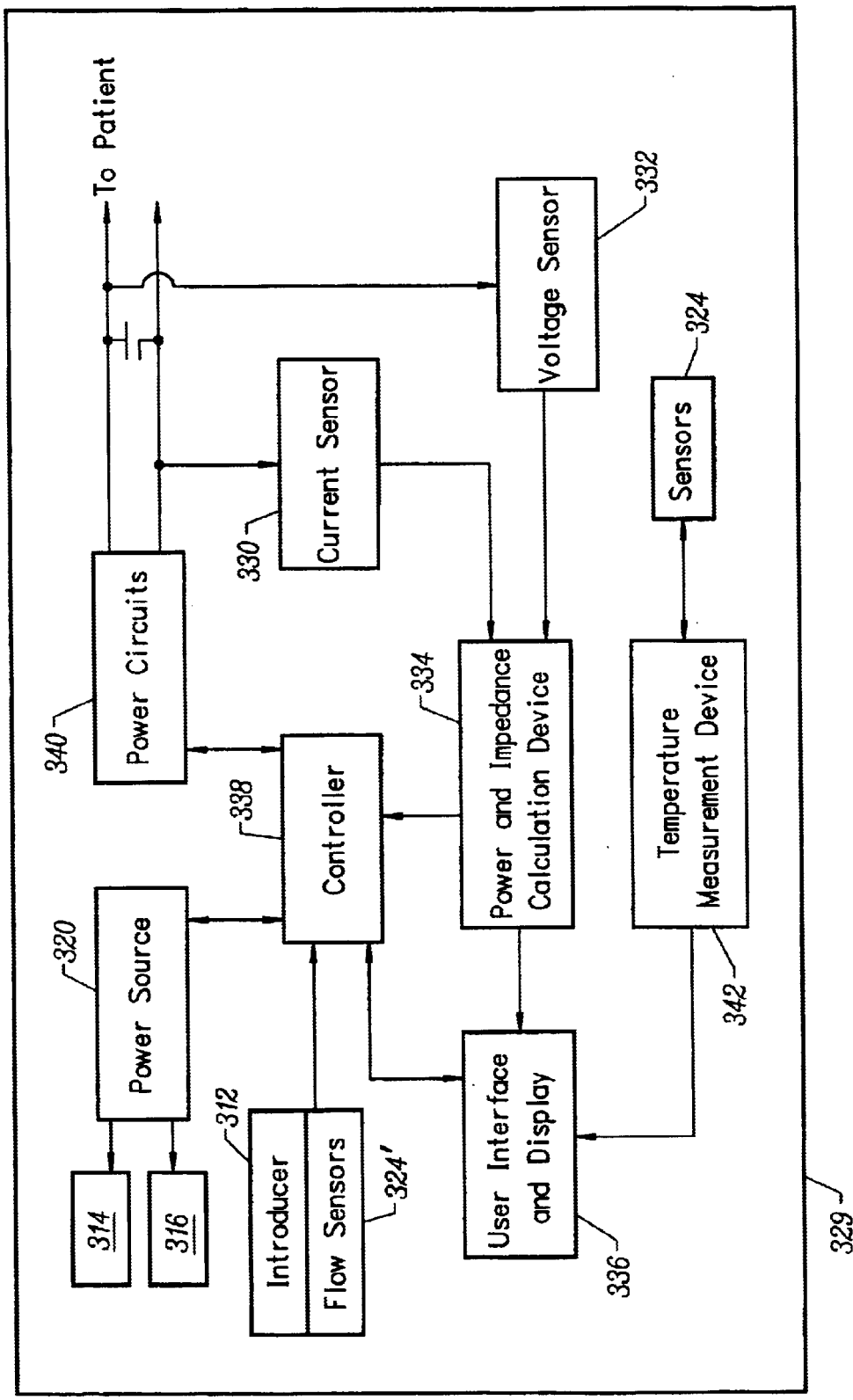
FIG. 27 is a block diagram illustrating the inclusion of a controller, energy source and other electronic components of the present invention.
Figure 28:
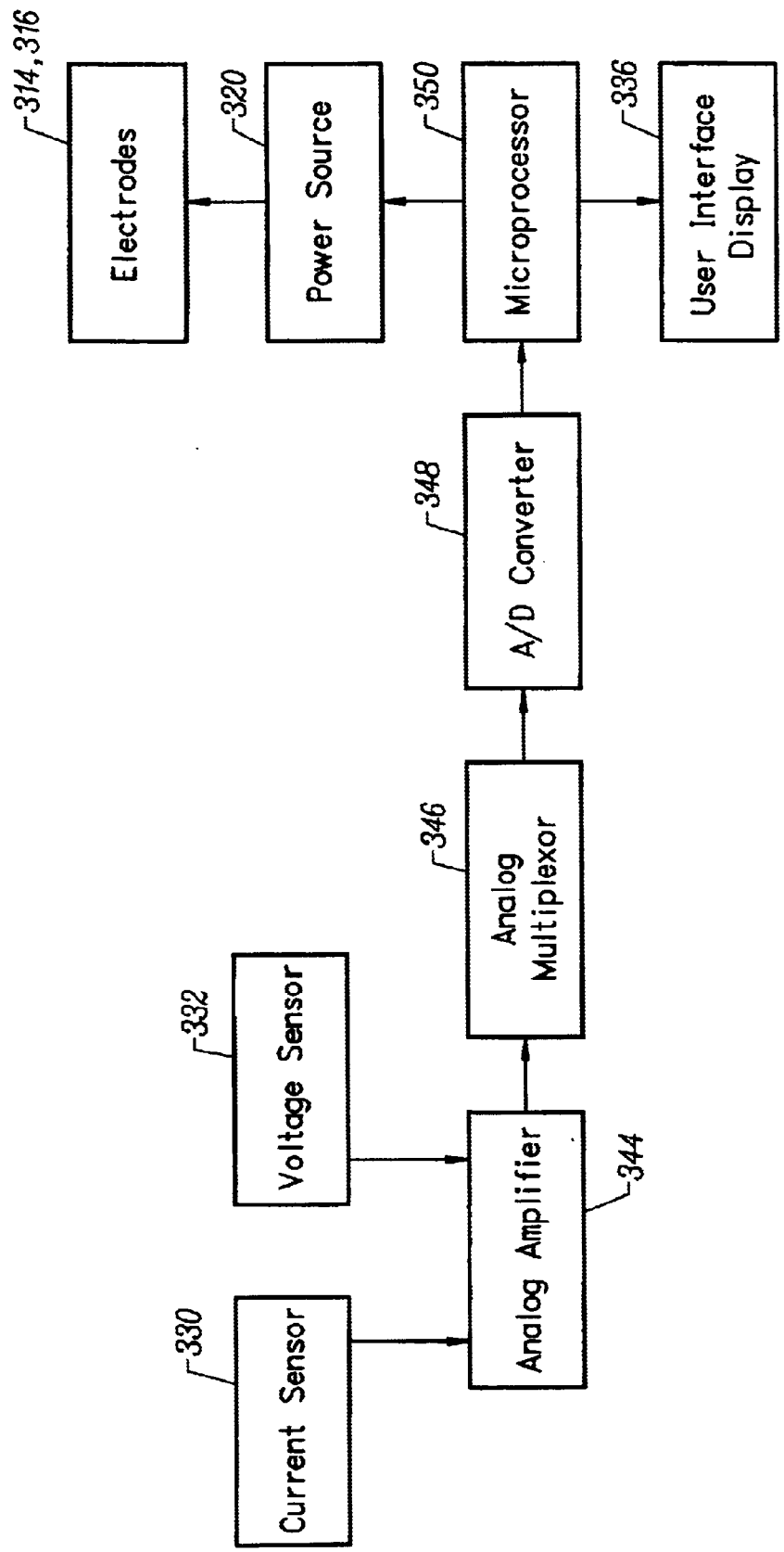
FIG. 28 is a block diagram illustrating an analog amplifier, analog multiplexer and microprocessor used with the present invention.

Referring now to FIGS. 27 and 28, a feedback control system 329 can be connected to energy source 320, sensors 324 and energy delivery devices 314 and 316. Feedback control system 329 receives temperature or impedance data from sensors 324 and the amount of electromagnetic energy received by energy delivery devices 314 and 316 is modified from an initial setting of ablation energy output, ablation time, temperature, and current density (the "Four Parameters"). Feedback control system 329 can automatically change any of the Four Parameters. Feedback control system 329 can detect impedance or temperature and change any of the Four Parameters. Feedback control system 329 can include a multiplexer to multiplex different antennas, a temperature detection circuit that provides a control signal representative of temperature or impedance detected at one or more sensors 324. A microprocessor can be connected to the temperature control circuit.

The following discussion pertains particularly to the use of an RF energy source and lung treatment/ablation apparatus 10. For purposes of this discussion, energy delivery devices 314 and 316 will now be referred to as RF electrodes/antennas 314 and 316 and energy source 320 will now be an RF energy source. However it will be appreciated that all other energy delivery devices and sources discussed herein are equally applicable and devices similar to those associated with lung treatment/ablation apparatus 10 can be utilized with laser optical fibers, microwave devices and the like. The temperature of the tissue, or of RF electrodes 314 and 316 is monitored, and the output power of energy source 320 adjusted accordingly. The physician can, if desired, override the closed or open loop system.

The user of apparatus 10 can input an impedance value that corresponds to a setting position located at apparatus 10. Based on this value, along with measured impedance values, feedback control system 329 determines an optimal power and time needed in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 316 from distal end 16' of introducer 12 to a position corresponding to a desired lesion size and monitoring the temperature at the periphery of the lesion such that a temperature sufficient to produce a lesion is attained. 37

The closed loop system 329 can also utilize a controller 338 to monitor the temperature, adjust the RF power, analyze the result, refeed the result, and then modulate the power. More specifically, controller 338 governs the power levels, cycles, and duration that the RF energy is distributed to electrodes 314 and 316 to achieve and maintain power levels appropriate to achieve the desired treatment objectives and clinical endpoints. Controller 338 can also in tandem govern the delivery of electrolytic, cooling fluid and, the removal of aspirated tissue. Controller 338 can also in tandem monitor for pressure leaks (via pressure flow sensors 324') through introducer 312 tending to cause pneumothorax and actuate coupled control valves to block the fluid path causing the leak and/or initiate the delivery of sealant X and/or energy at the target tissue site to seal the leak. Controller 338 can be integral to or otherwise coupled to power source 320. The controller 338 can be also be coupled to an input/output (I/O) device such as a keyboard, touchpad, PDA, microphone (coupled to speech recognition software resident in controller 338 or other computer) and the like.

Referring now to FIG. 27, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334.

These values can then be displayed at a user interface and display 336. Signals representative of power and impedance values are received by controller 338 which can be a microprocessor 339.

A control signal is generated by controller 338 that is proportional to the difference between an actual measured value, and a desired value. The control signal is used by power circuits 340 to adjust the power output in an appropriate amount in order to maintain the desired power delivered at the respective primary and/or secondary antennas 314 and 316. In a similar manner, 30 temperatures detected at sensors 324 provide feedback for maintaining a selected power. The actual temperatures are measured at temperature measurement device 342, and the temperatures are displayed at user interface and display 336. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensor 324. A multiplexer 346 can be included to measure current, voltage and temperature, at the numerous sensors 324 as well as deliver and distribute energy between primary electrodes 314 and secondary electrodes 316.

Controller 338 can be a digital or analog controller, or a computer with embedded, resident or otherwise coupled software. In an embodiment controller 338 can be a Pentium® family microprocessor manufacture by the Intel® Corporation (Santa Clara, Calif.). When controller 338 is a computer it can include a CPU coupled through a system bus. On this system can be a keyboard, a disk drive, or other non-volatile memory systems, a display, and other peripherals, as are known in the art. Also coupled to the bus are a program memory and a data memory. In various embodiments controller 338 can be coupled to imaging systems, including but not limited to ultrasound, CT scanners (including fast CT scanners such as those manufacture by the Imatron Corporation (South San Francisco, Calif.), X-ray, MRI, mammographic X-ray and the like. Further, direct visualization and tactile imaging can be utilized.

User interface and display 336 can include operator controls and a display. In an embodiment user interface 336 can be a PDA device known in the art such as a Palm® family computer manufactured by Palm® Computing (Santa Clara, Calif.). Interface 336 can be configured to allow the user to input control and processing variables, to enable the controller to generate appropriate command signals. Interface 336 can also receives real time processing feedback information from one or more sensors 324 for processing by controller 338, to govern the delivery and distribution of energy, fluid etc.

The output of current sensor 330 and voltage sensor 332 is used by controller 338 to maintain a selected power level at primary and secondary antennas 314 and 316. The amount of RF energy delivered controls the amount of power. A profile of power delivered can be incorporated in controller 338, and a preset amount of energy to be delivered can also be profiled.

Circuitry, software and feedback to controller 338 results in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 324. A controller 338 can be incorporated into feedback control system 329 to switch power on and off, as well as modulate the power. Also, with the use of sensor 324 and feedback control system 329, tissue adjacent to RF electrodes 314 and 316 can be maintained at a desired temperature for a selected period of time without causing a shut down of the power circuit to electrode 314 due to the development of excessive electrical impedance at electrode 314 or adjacent tissue.

Referring now to FIG. 28, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage which represents the respective sensed temperatures. Digitized amplifier output voltages are supplied by A/D converter 348 to a microprocessor 350. Microprocessor 350 may be Model No. 68HCII available from Motorola. However, it will be appreciated that any suitable microprocessor or general purpose digital or analog computer can be used to calculate impedance or temperature.

Microprocessor 350 sequentially receives and stores digital representations of impedance and temperature. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with power and impedance limits. When the values exceed predetermined power or impedance values, a warning can be given on user interface and display 336, and additionally, the delivery of RF energy can be reduced, modified or interrupted. A control signal from microprocessor 350 can modify the power level supplied by energy source 320 to RF electrodes 314 and 316. In a similar manner, temperatures detected at sensors 324 provide feedback for determining the extent and rate of (i) tissue hyperthermia (ii) cell necrosis; and (iii) when a boundary of desired cell necrosis has reached the physical location of sensors 324.

The apparatus and method of this invention provide a more precise, controlled medical treatment which is suitable for obtaining biopsy tissue samples and ablating medically targeted tissues throughout the body, both within and external to body organs. The apparatus and method are particularly useful for obtaining biopsy tissue samples and treating the lung for various diseases including benign and cancerous tumors. It will be readily apparent to a person skilled in the art that various embodiments and combinations of embodiments of the device and method can be used to sample or ablate/destroy body tissues, tissue locations that are accessible by percutaneous or endoscopic catheters, and is not limited to the lung. Such tissue locations and organs include, but are not limited to, the heart and cardiovascular system, upper respiratory tract and gastrointestinal system. Application of the apparatus and method in all of these organs and tissues are intended to be included within the scope of this invention.

Also this specification discloses various catheter-based systems and methods for treating the lung and adjoining tissue regions in the body. The systems and methods that embody features of the invention are also adaptable for use with systems and surgical techniques both in the lung and other areas of the body that are not necessarily catheter-based. Furthermore, this specification is not intended to be exhaustive or to limit the invention to the precise forms disclosed. Obviously, many modifications, variations and different combinations of embodiments will be apparent to practitioners skilled in this art. Also, elements from one embodiment can be readily recombined with one or more other embodiments.

The foregoing description of a preferred embodiment of the invention has been presented for purposes of illustration and description. It is intended that the scope of the invention be defined by the following claims and their equivalents.

What is claimed is:

1. An improved ablation apparatus for lung treatment said apparatus having an elongated member including a lumen and a tissue piercing distal end, and an energy delivery device being positionable in said elongated member and including at least one electrode operatively coupled to a power source, the improvement comprising:
   a lung biopsy device comprising a needle for obtaining a core sample; and
   at least one sensor coupled to the elongated member;
   wherein said energy delivery device is operatively coupled to the power source.

2. The apparatus of claim 1, wherein the sensor is coupled to one of an elongated member distal end, or the elongated member lumen.

3. The apparatus of claim 1, wherein the elongated member lumen terminates in at least one aperture for fluid delivery.

4. The apparatus of claim 3, further comprising:
   a fluid source coupled to the elongated member lumen for fluid delivery to the at least one aperture.

5. The apparatus of claim 4, wherein said fluid source is coupled to feedback control resources or a control valve for controlling fluid delivery.

6. The apparatus of claim 4, wherein the fluid source includes a fluid delivery device.

7. The apparatus of claim 4, wherein the fluid source is selected from a gas source, a liquid source, a liquid polymer source, and an electrolytic solution source.

8. The apparatus of claim 7, wherein the liquid polymer is a curable liquid polymer selected from heat curable, chemically curable, and photactivated curable.

9. The apparatus of claim 7, wherein the liquid polymer has a viscoelestatic property alterable by an activating agent.

10. The apparatus of claim 4, wherein one of the elongated member lumen or the at least one aperture includes a valve selected from the group consisting of a one way valve, a control valve, and a control valve coupled to feedback control resources.

11. The apparatus of claim 7, wherein the liquid polymer source includes one of an elastomer, a collagen, a silicone, a bioabsorbably polymers, or a hydrogel.

12. The apparatus of claim 4, wherein the fluid source is an electrolytic solution delivered to the target tissue to create a fluid volume, to create an enhanced electrode.

13. The apparatus of claim 3, wherein the at least one aperture is a plurality of apertures.

14. The apparatus of claim 13, wherein the plurality of apertures are at the distal end of the elongated member.

15. The apparatus of claim 13, wherein the plurality of apertures are configured to deliver one of a fluid, a conductive fluid, or a cooling fluid to at least one of the energy delivery device or the target tissue.

16. The apparatus of claim 1, wherein the sensor is selected from the group consisting of a pressure sensor, a force sensor, a flow sensor, a thermal sensor, an acoustical sensor, an impedance sensor, and an optical sensor.

17. The apparatus of claim 1, wherein the sensor is operably coupled to detect one of an opening, a fluidic opening, a tear, a seal, a hermetic seal or a closure of the tissue void.

18. The apparatus of claim 1, wherein the sensor is detects a pressure differential.

19. The apparatus of claim 1, wherein the sensor is detects a fluid flow rate.

20. The apparatus of claim 1, wherein the at least one sensor comprises a plurality of sensors.

21. The apparatus of claim 1, wherein the at least one sensor comprises a first sensor and a second sensor, said second sensor having a more distal position on the elongated member with respect to the first sensor.

22. The apparatus of claim 1, wherein the elongate member distal end has one of an atraumatic surface, an atraumatic coating, or a lubricious coating.

23. The apparatus of claim 1, further comprising an advancement and retraction member coupled to the biopsy device.

24. The apparatus of claim 1, further comprising:
at least one sensor coupled to the biopsy device.

25. The apparatus of claim 1, further comprising a valve coupled to at least one of the elongated member, or the lung biopsy device.

26. The apparatus of claim 25, wherein the valve is a control valve.

27. The apparatus of claim 25, wherein the valve is a disc movably coupled to one of the elongated member, or the lung biopsy device.

28. The apparatus of claim 25, wherein the valve is a constrictable valve.

29. The apparatus of claim 28, wherein the constrictable valve comprises at least a portion of the elongated member, or the lung biopsy device.

30. The apparatus of claim 1, further comprising:
a handpiece coupled to a proximal portion of the elongated member.

31. The apparatus of claim 30, further wherein the handpiece includes one of a fitting, an infusion port, a lumen, or a deflection mechanism.

32. The apparatus of claim 1, wherein the energy delivery device is an RF electrode.

33. The apparatus of claim 32, wherein the RF electrode is selected from the group consisting of a ring electrode, a conical shaped electrode, a needle electrode and a porous electrode.

34. The apparatus of claim 32, wherein the at least one electrode is selected from a plurality of electrodes, an array of electrodes, an array of monopolar electrodes, an array of bipolar electrodes, and an array of multiplexed electrodes.

35. (currently amended) The apparatus of claim 34, further comprising:
a multiplexing device coupled to at least a portion of the plurality of electrodes and, the power supply.

36. The apparatus of claim 1, further comprising:
a ground pad electrode coupled to the skin and coupled to the power supply.

37. The apparatus of claim 36, further comprising:
feedback control resources coupled to at least one of the power supply, the energy delivery device, and the sensor.

38. The apparatus of claim 1, wherein the at least one electrode comprises a first set of electrodes, each electrode of the first set having a tissue piercing distal end and being positionable in the elongated member as the elongated member is advanced through tissue, the first set of electrodes being deployable with curvature from the elongated member.

39. The apparatus of claim 38, wherein the at least one electrode comprises a second set of electrodes, each electrode of the second set having a tissue piercing distal end and being positionable in the elongated member as the elongated member is advanced through tissue, the second set of RF electrodes being deployable with curvature from the elongated member.

40. The apparatus of claim 39, wherein the second set of RF electrodes being deployable a greater distance than the first set of electrodes.

41. The apparatus of claim 39, wherein at least one of the first or the second set of electrodes is deployable with at least one radius of curvature.

42. The apparatus of claim 1, further comprising:
a closure device coupled to the elongated member, the closure device configured to substantially close a tissue void space within the lung.

43. The apparatus of claim 42, wherein the closure device has a non-deployed state and a deployed state, the closure device being deliverable to the tissue void space in the non deployed state and put into the deployed state to engage tissue substantially adjacent the void space and substantially close the void space.

44. The apparatus of claim 43, wherein the closure device is detachable from the elongated member in one of the deployed state or the non-deployed state.

45. The apparatus of claim 44, wherein the closure device is deployable before detachment from the elongated member.

46. The apparatus of claim 44, wherein the closure device is deployable after detachment from the elongated member.

47. The apparatus of claim 43, wherein the closure device is selected from a spring device, a coiled spring, a tapered spring, a surgical staple, a suture, a mesh, a plug, a shaped plug, an expandable plug, and a plurality of mechanical coupled curved wires having tissue piercing distal tips.

48. The apparatus of claim 42, wherein the closure device is disposed within the elongated member lumen.

49. The apparatus of claim 42, wherein the closure device is configured to seal or substantially hermetically seal the tissue void.

50. The apparatus of claim 42, wherein the closure device is configured to prevent a pneumothorax through the tissue void space.

51. The apparatus of claim 42, wherein at least a portion of the closure device comprises at least one of a polymer, an elastomer, a bioabsorbable polymer, a metal alloy, or a shape memory alloy.

52. The apparatus of claim 42, wherein at least a portion of the closure device is curable in situ.

53. The apparatus of claim 52, wherein the at least a portion of the closure device is curable via the delivery of energy from the energy delivery device.

54. The apparatus of claim 42, wherein at least a portion of the closure device includes at least one of an imagable marker, a radio-opaque marker, or an echogenic marker.

55. The apparatus of claim 42, further comprising:
a sensor coupled to the elongated member, wherein the sensor detects a property of the lung.

56. The apparatus of claim 55, wherein the sensor is coupled to at least one of the elongated member distal end, the energy delivery device, the closure device, or the elongated member lumen.

57. The apparatus of claim 55, wherein the sensor is selected from the group consisting of a pressure sensor, a force sensor, a flow sensor, a thermal sensor, an acoustical sensor, an impedance sensor and an optical sensor.

58. The apparatus of claim 55, wherein the sensor is configured to detect one of an opening, a fluidic opening, a tear, a seal, a hermetic seal or a closure of the tissue void.

59. (original) The apparatus of claim 55, where in the sensor is configured to detect a pressure differential.

60. The apparatus of claim 42, wherein the sensor is configured to detect a fluid flow rate.

61. The apparatus of claim 1, wherein the lung biopsy device has a distal end that is configured to cut and collect a lung tissue sample.

62. The apparatus according to claim 1, wherein the power source is a RF power source.

63. The apparatus according to claim 62, further comprising:
a feedback control device operatively coupled to said sensor and the RF power source to control application of RF current to the at least one electrode.

64. The apparatus according to claim 1, wherein said lung biopsy device is selected from the group consisting of a lung biopsy needle, a tissue aspiration device, and a tissue collection device.

65. The apparatus according to claim 64, wherein when said lung biopsy device is a tissue aspiration device or a tissue collection device, the device is selected from the group consisting of a syringe, a vacuum source operatively coupled to a filter, and a vacuum source operatively coupled to a collection chamber.

66. The apparatus according to claim 1, further including a deflection mechanism operatively coupled to said elongated member for deflecting and steering said elongated member.

67. The apparatus according to claim 66, wherein said deflection mechanism is selected from the group consisting of a pull wire, a ratchet, a latch and lock mechanism, and a piezoelectric material.

68. The apparatus according to claim 1, wherein said elongated member is coated with a lubricious coating or a film.

69. The apparatus according to claim 1, further comprising a second lung biopsy device.

70. The apparatus according to claim 1, further comprising a ground pad electrode.

71. The apparatus according to claim 1, further comprising an imaging system operatively coupled to the elongated member.

72. The apparatus according to claim 1, further comprising one of an introducing device, a percutaneous introducing device, and a trocar for positioning said elongated member at said tissue site.

* * * * *

UNITED STATES PATENT AND TRADEMARK OFFICE
CERTIFICATE OF CORRECTION

PATENT NO. : 6,770,070 B1 Page 1 of 1
DATED : August 3, 2004
INVENTOR(S) : Daniel J. Balbierz It is certified that error appears in the above-identified patent and that said Letters Patent is hereby corrected as shown below:

Title page,
Item [73], Assignee, please replace "R. ITA" with -- RITA --.

Signed and Sealed this

Twenty-second Day of November, 2005

JON W. DUDAS
*Director of the United States Patent and Trademark Office*